United States Patent
Azizian et al.

(10) Patent No.: US 10,064,682 B2
(45) Date of Patent: *Sep. 4, 2018

(54) COLLISION AVOIDANCE DURING CONTROLLED MOVEMENT OF IMAGE CAPTURING DEVICE AND MANIPULATABLE DEVICE MOVABLE ARMS

(71) Applicant: Intuitive Surgical Operations, Inc., Sunnyvale, CA (US)

(72) Inventors: Mahdi Azizian, Sunnyvale, CA (US); Jonathan Sorger, Belmont, CA (US); Lutz Blohm, Mohrendorf (DE); Christine Niebler, Ruckersdorf (DE); Holger Kunze, Bubenreuth (DE)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 358 days.

This patent is subject to a terminal disclaimer.

(21) Appl. No.: 14/862,692

(22) Filed: Sep. 23, 2015

(65) Prior Publication Data

US 2016/0008078 A1 Jan. 14, 2016

Related U.S. Application Data

(63) Continuation of application No. 14/101,769, filed on Dec. 10, 2013, now Pat. No. 9,259,282.

(Continued)

(51) Int. Cl.
*A61B 5/00* (2006.01)
*A61B 19/00* (2006.01)
(Continued)

(52) U.S. Cl.
CPC .......... *A61B 19/2203* (2013.01); *A61B 6/102* (2013.01); *A61B 6/4441* (2013.01);
(Continued)

(58) Field of Classification Search
CPC ..... A61B 19/2203; A61B 34/20; A61B 34/30; A61B 6/102; A61B 6/4441; A61B 6/4458;
(Continued)

(56) References Cited

U.S. PATENT DOCUMENTS 4,578,757 A 3/1986 Stark
4,644,237 A 2/1987 Frushour et al.
(Continued)

FOREIGN PATENT DOCUMENTS

CN 102523737 A 6/2012
EP 2468207 A1 6/2012
(Continued)

OTHER PUBLICATIONS

Extended European Search Report for Application No. 13862685.8, dated Sep. 19, 2016, 14 pages.
(Continued)

*Primary Examiner* — Nicholas Kiswanto

(57) ABSTRACT

A system and method for movement control includes a controller coupled to a computer-assisted surgical device having a first movable arm coupled to a manipulatable device having a working end and a second movable arm coupled to an image capturing device. The controller is configured to receive first configurations for the first movable arm; receive second configurations for the second movable arm; receive a plurality of images of the working end from the image capturing device; determine a position and an orientation of the working end; determine a first movable arm position and trajectory for the first movable arm; determine a second movable arm position and trajectory for the second movable arm; determine whether motion of the movable arms will result in an undesirable relationship between the movable arms; and send a movement (Continued)

command to the first or second movable arm to avoid the undesirable relationship.

20 Claims, 14 Drawing Sheets

Related U.S. Application Data

(60) Provisional application No. 61/735,170, filed on Dec. 10, 2012.

(51) Int. Cl.
| | |
|---|---|
| *B25J 9/16* | (2006.01) |
| *A61B 6/00* | (2006.01) |
| *A61B 34/20* | (2016.01) |
| *A61B 34/30* | (2016.01) |
| *A61B 6/10* | (2006.01) |
| *A61B 90/00* | (2016.01) |

(52) U.S. Cl.
CPC ............ *A61B 6/4458* (2013.01); *A61B 34/20* (2016.02); *A61B 34/30* (2016.02); *B25J 9/1676* (2013.01); *B25J 9/1697* (2013.01); *A61B 90/37* (2016.02); *A61B 2034/2055* (2016.02); *A61B 2034/2059* (2016.02); *A61B 2034/2065* (2016.02); *A61B 2090/376* (2016.02); *A61B 2090/378* (2016.02); *Y10S 901/02* (2013.01); *Y10S 901/47* (2013.01)

(58) Field of Classification Search
CPC .... A61B 2034/2055; A61B 2034/2059; A61B 2034/2065; A61B 90/37; A61B 2090/376; A61B 2090/378; Y10S 901/02; Y10S 901/47; B25J 9/1676; B25J 9/1697
See application file for complete search history.

(56) References Cited

U.S. PATENT DOCUMENTS

| | | | |
|---|---|---|---|
| 5,737,500 A * | 4/1998 | Seraji ................... | B25J 9/1643 318/568.11 |
| 6,659,939 B2 | 12/2003 | Moll et al. | |
| 6,678,582 B2 | 1/2004 | Waled | |
| 6,788,018 B1 | 9/2004 | Blumenkranz | |
| 7,046,765 B2 | 5/2006 | Wong et al. | |
| 7,379,533 B2 | 5/2008 | Koertge | |
| 7,428,296 B2 | 9/2008 | Bernhardt et al. | |
| 7,446,304 B2 | 11/2008 | Li | |
| 7,564,949 B2 | 7/2009 | Sattler et al. | |
| 7,725,214 B2 | 5/2010 | Diolaiti | |
| 8,004,229 B2 * | 8/2011 | Nowlin ................. | B25J 9/1682 318/568.21 |
| 8,108,072 B2 | 1/2012 | Zhao et al. | |
| 8,170,716 B2 | 5/2012 | Coste-Maniere et al. | |
| 9,259,282 B2 | 2/2016 | Azizian et al. | |
| 9,259,289 B2 | 2/2016 | Zhao et al. | |
| 9,775,681 B2 * | 10/2017 | Quaid .................... | A61B 34/30 |
| 9,789,608 B2 * | 10/2017 | Itkowitz ................ | B25J 9/1666 |
| 2006/0149418 A1 | 7/2006 | Anvari | |
| 2007/0021738 A1 | 1/2007 | Hasser et al. | |
| 2007/0167702 A1 | 7/2007 | Hasser et al. | |
| 2008/0037712 A1 | 2/2008 | Klingenbeck-Regn | |
| 2009/0003975 A1 * | 1/2009 | Kuduvalli ............. | A61N 5/1049 414/146 |
| 2009/0177081 A1 | 7/2009 | Joskowicz et al. | |
| 2009/0192524 A1 * | 7/2009 | Itkowitz ................ | B25J 9/1666 606/130 |
| 2009/0234444 A1 | 9/2009 | Maschke | |
| 2009/0268010 A1 | 10/2009 | Zhao et al. | |
| 2009/0326553 A1 | 12/2009 | Mustufa et al. | |
| 2010/0168763 A1 | 7/2010 | Zhao et al. | |
| 2010/0331855 A1 | 12/2010 | Zhao et al. | |
| 2010/0332031 A1 | 12/2010 | Itkowitz et al. | |
| 2011/0066282 A1 | 3/2011 | Bosscher et al. | |
| 2011/0276179 A1 | 11/2011 | Banks et al. | |
| 2012/0022689 A1 | 1/2012 | Kapoor | |
| 2012/0053597 A1 | 3/2012 | Anvari et al. | |
| 2012/0059392 A1 | 3/2012 | Diolaiti | |
| 2012/0182392 A1 * | 7/2012 | Kearns .................. | B25J 11/009 348/46 |
| 2012/0221011 A1 | 8/2012 | Larkin et al. | |
| 2012/0290134 A1 | 11/2012 | Zhao et al. | |
| 2013/0281818 A1 * | 10/2013 | Vija ...................... | A61B 6/467 600/407 |
| 2014/0163736 A1 | 6/2014 | Azizian et al. | |
| 2016/0206387 A1 | 7/2016 | Zhao et al. | |

FOREIGN PATENT DOCUMENTS

| | | |
|---|---|---|
| JP | 2011206312 A | 10/2011 |
| WO | WO-2011125007 A1 | 10/2011 |
| WO | WO-2012158458 A2 | 11/2012 |

OTHER PUBLICATIONS

Partial Supplementary European Search Report for Application No. 13862685.8, dated May 27, 2016, 10 pages.
International Search Report and Written Opinion for Application No. PCT/US2013/074163, dated Mar. 31, 2014, 11 pages.
Ladikos A., et al., "Real-Time 3D Reconstruction for Collision Avoidance in Interventional Environments", Metaxas D., et al., Eds., MICCAI 2008, Part II, LNCS 5242, Springer-Verlag Berlin Heidelberg, 2008, pp. 526-534.
Morvan T., et al., "Collision Detection and Untangling for Surgical Robotic Manipulators," The International Journal of Medical Robotics and Computer Assisted Surgery, 2009, vol. 5, pp. 233-242.
Ramezanifard R., et al., "A Novel Modeling Approach for Collision Avoidance in Robotic Surgery," American Journal of Applied Sciences, 2007, vol. 4 (9), pp. 693-699.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

COLLISION AVOIDANCE DURING CONTROLLED MOVEMENT OF IMAGE CAPTURING DEVICE AND MANIPULATABLE DEVICE MOVABLE ARMS

CROSS-REFERENCE TO RELATED APPLICATIONS

This application is a continuation of U.S. patent application Ser. No. 14/101,769, filed Dec. 10, 2013 and claims priority to U.S. Provisional Application No. 61/735,170, filed Dec. 10, 2012, entitled "Collision Avoidance During Controlled Movement of Image Capturing Device and Manipulatable Robot Arms", both of which are incorporated herein in their entirety by reference.

FIELD OF THE INVENTION

The present invention generally relates to robotic systems and in particular, to collision avoidance during controlled movement of image capturing device and manipulatable device robot arms.

BACKGROUND OF THE INVENTION

Robotic systems and computer-assisted devices often include robot or movable arms to manipulate instruments for performing a task at a work site and at least one robot or movable arm for supporting an image capturing device which captures images of the work site. When the robot arms are operating within close proximity to each other, there is a possibility that the arms may collide with one another and by so doing, cause damage to the arms. When the robot arms are commonly operated, preventing such collisions may be straightforward. However, when the robot arms are independently operated, collision avoidance may be much more challenging.

A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

To avoid collisions between robot arms it is useful to have information of the configurations of the arms and information of their respective positions in a common reference frame. With this information, a controller that is controlling the movement of one of the robot arms can take action to avoid a collision with another robot arm.

One action that the controller may take to avoid collisions is to warn an operator who is commanding a robot arm that a collision with another robot arm is imminent. As one example of such a warning system, U.S. 2009/0192524 A1 entitled "Synthetic Representation of a Surgical Robot," which is incorporated herein by reference, describes a patient side cart upon which a plurality of robot arms is mounted. As another example of such a warning system, U.S. 2009/0326553 entitled "Medical Robotic System Providing an Auxiliary View of Articulatable Instruments Extending out of a Distal End of an Entry Guide," which is incorporated herein by reference, describes a medical robotic system having a plurality of articulated instruments extending out of an entry guide. As yet another example of such a warning system, U.S. 2009/0234444 A1 entitled "Method and Apparatus for Conducting an Interventional Procedure Involving Heart Valves using a Robot-based X-ray Device," which is incorporated herein by reference, describes a medical robotic system in which an X-ray source and detector are mounted on opposing ends of a C-arm so that X-ray images of a patient's anatomy can be captured during the performance of a medical procedure using a catheter control robot.

Collision avoidance may also be performed automatically by a controller which is controlling movement of one or more robot arms. As an example of such an automatic collision avoidance system, U.S. Pat. No. 8,004,229 entitled "Software center and highly configurable robotic systems for surgery and other uses," which is incorporated herein by reference, describes a medical robotic system that is configured to avoid collisions between its robot arms. The robot arms have redundancy so that multiple configurations are possible for each arm to achieve a desired position and orientation of its held instrument. Each controller commands movement of its associated robot arm subject to a secondary constraint that results in eliminating possible arm configurations that would result in a collision with another robot arm.

When a plurality of robot arms is controlled by a plurality of controllers, however, confusion and unintended consequences may result if more than one of the plurality of controllers is attempting to avoid collisions. This problem is exacerbated when there is none or only limited communication of information between the controllers, such as may be the case when the robotic system employs independently operated robot arms. To avoid robot arm collision problems, the independently operated robot arms may be used sequentially, but not concurrently at the work site. However, it may be advantageous to use the robot arms concurrently during the performance of a procedure or task at a work site.

OBJECTS AND SUMMARY OF THE INVENTION

Accordingly, one object of one or more aspects of the present invention is a robotic system and method implemented therein that automatically performs collision avoidance of robot arms.

Another object of one or more aspects of the present invention is a robotic system and method implemented therein that automatically performs collision avoidance of independently operated robot arms.

Another object of one or more aspects of the present invention is a robotic system and method implemented therein that automatically performs collision avoidance of robot arms without preventing any of the robot arms from performing its intended task.

These and additional objects are accomplished by the various aspects of the present invention, wherein briefly stated, one aspect is a robotic system including: a first robot arm holding a manipulatable device having a working end; and a controller configured to control movement of at least one of the first robot arm and a second robot arm while avoiding a collision between the first and second robot arms, wherein the second robot arm holds an image capturing device for capturing a plurality of images of the working end of the manipulatable device from which a three-dimensional computer model of the working end of the manipulatable device is generatable; wherein the controller is configured to avoid the collision between the first and second robot arms:

by determining a position and an orientation of the working end of the manipulatable device relative to a reference frame of the image capturing device by using at least one image of the plurality of images of the working end of the manipulatable device, wherein the reference frame of the image capturing device corresponds to a perspective of the captured images; by determining a configuration and position of one of the first and second robot arms relative to a common reference frame by using the determined position and orientation of the working end of the manipulatable device relative to the reference frame of the image capturing device; and by determining a configuration and position of the other of the first and second robot arms relative to the common reference frame by using joint position information received for the other of the first and second robot arms; by determining an imminent collision between the first and second robot arms using the determined configurations and positions of the first and second robot arms relative to the common reference frame; and by commanding an action to be taken by one of the first and second robot arms to avoid the imminent collision.

Another aspect is a method implemented in a robotic system for avoiding collisions between first and second robot arms, wherein the first robot arm holds a manipulatable device having a working end, wherein the second robot arm holds an image capturing device for capturing a plurality of images of the working end of the manipulatable device from which a three-dimensional computer model of the working end of the manipulatable device is generatable, and wherein the method includes: determining a position and an orientation of the working end of the manipulatable device relative to a reference frame of the image capturing device by using at least one image of the plurality of images of the working end of the manipulatable device, wherein the reference frame of the image capturing device corresponds to a perspective of the captured images; determining a configuration and position of one of the first and second robot arms relative to a common reference frame by using the determined position and orientation of the working end of the manipulatable device relative to the reference frame of the image capturing device; determining a configuration and position of the other of the first and second robot arms relative to the common reference frame by using joint position information received for the other of the first and second robot arms; determining an imminent collision between the first and second robot arms using the determined configurations and positions of the first and second robot arms relative to the common reference frame; and commanding an action to be taken by one of the first and second robot arms to avoid the imminent collision.

Another aspect is a robotic system including: a first robot arm that is holding a manipulatable device having a working end; and a processor programmed to register the first robot arm to a second robot arm that is holding an image capturing device, wherein the processor performs the registration by: performing a low accuracy registration of the first and second robot arms at initial positions of the first and second robot arms using external tracking data and kinematics data of at least one of the first and second robot arms; performing a mid accuracy registration of the first and second robot arms relative to a first setup position using at least one image captured by the image capturing device of at least a part of the first robot arm and kinematics data of at least one of the first and second robot arms, wherein the first setup position includes a first safety margin indicative of the low accuracy registration; and performing a high accuracy registration of the first and second robot arms relative to a second setup position using at least one image captured by the image capturing device of the working end of the manipulatable device and kinematics data of at least one of the first and second robot arms, wherein the second setup position includes a second safety margin indicative of the mid accuracy registration.

Another aspect is a method implemented by a processor for registering first and second robot arms. The first robot arm holds a manipulatable device having a working end. The second robot arm holds an image capturing device. The method includes performing a low accuracy registration of the first and second robot arms at initial positions of the first and second robot arms using external tracking data and kinematics data of at least one of the first and second robot arms; performing a mid accuracy registration of the first and second robot arms relative to a first setup position using at least one image captured by the image capturing device of at least a part of the first robot arm and kinematics data of at least one of the first and second robot arms, wherein the first setup position includes a first safety margin indicative of the low accuracy registration; and performing a high accuracy registration of the first and second robot arms relative to a second setup position using at least one image captured by the image capturing device of the working end of the manipulatable device and kinematics data of at least one of the first and second robot arms, wherein the second setup position includes a second safety margin indicative of the mid accuracy registration.

Consistent with some embodiments, a movement control system includes a controller. The controller includes one or more processors and memory coupled to the one or more processors. The controller is coupled to a computer-assisted surgical device having a first movable arm coupled to a manipulatable device having a working end. The controller is further coupled to a second movable arm coupled to an image capturing device separate from the computer-assisted surgical device. The controller is configured to receive one or more first configurations for the first movable arm; receive one or more second configurations for the second movable arm; receive a first plurality of images of the working end from the image capturing device; determine, based on at least one of the first plurality of images, a position and an orientation of the working end in a common reference frame; determine, based on the first configurations, a first movable arm position and a first movable arm trajectory for the first movable arm in the common reference frame; determine, based on the second configurations, a second movable arm position and a second movable arm trajectory for the second movable arm in the common reference frame; based on the first movable arm position, the first movable arm trajectory, the second movable arm position, and the second movable arm trajectory, determine whether motion of the first movable arm, motion of the second movable arm, or motions of the first and second movable arms together will result in an undesirable relationship between the first and second movable arms; and send a first movement command to the first movable arm or the second movable arm to avoid the undesirable relationship.

In some examples, the common reference frame is a reference frame of the image capturing device and the controller is further configured to determine the first movable arm position in the common reference frame further based on the position and the orientation of the working end in the common reference frame. In some examples, the common reference frame is a reference frame of the computer-assisted surgical device and the controller is further configured to determine the second movable arm position in a reference frame of the image capturing device, determine the position and the orientation of the working end in the reference frame of the image capturing device, and transform the second movable arm position and the position and orientation of the working end from the reference frame of the image capturing device to the common reference frame.

In some examples, the first plurality of images are a plurality of two-dimensional images from a image capturing device and the controller is further configured to determine the position and the orientation of the working end from the two-dimensional images even when the working end of the manipulatable device is occluded by one or more objects disposed between the image capturing device and the working end of the manipulatable device. In some examples, the system further includes a viewer adapted to display a second plurality images of a work space of the working end of the manipulatable device and an input unit configured to receive information of a user specified region of interest within the images being displayed on the viewer. The controller is further configured to send second movement commands to the second movable arm so that the image capturing device captures images of the user specified region of interest.

In some examples, the input unit includes a gaze tracking unit configured to track a gaze of a user on a display screen of the viewer and the gaze tracking unit includes an indicator operable by the user to indicate the region of interest by using a current gaze point of the user on the display screen. In some examples, the input unit includes a telestrator unit configured to receive one of the second plurality of images and display the received one of the second plurality of images on a display screen of the telestrator and the telestrator unit includes a marker unit operable by a user to indicate the region of interest on the displayed one of the second plurality of images.

In some examples, the system further includes a camera, and the second plurality of images are captured by the camera. In some examples, system further includes an ultrasound probe, and the second plurality of images are captured by the ultrasound probe. In some examples, the first movable arm has redundant degrees of freedom so that for each controllable position and orientation of the working end of the manipulatable device there are a first plurality of possible positions and orientations for the first movable arm, the second movable arm has redundant degrees of freedom so that for each controllable position and orientation of the image capturing device there are a second plurality of possible positions and orientations for the second movable arm, and the first movement command sent to the first movable arm or the second movable arm directs the first movable arm to move to one of the first plurality of possible positions and orientations or directs the second movable arm to move to one of the second plurality of possible positions and orientations that avoid the undesirable relationship.

In some examples, the controller is further configured to determine which one of the first movable arm and the second movable arms is to be sent the first movement command based on differences between the first movable arm position and the first plurality of possible positions and orientations and differences between the second movable arm position and the second plurality of possible positions and orientations and the determination is made so as to minimize a cost function.

In some examples, the first movement command directs the first movable arm to move from the first movable arm position to a first selected one of the first plurality of possible positions and orientations or directs the second movable arm to move from the second movable arm position to a second selected one of the second plurality of possible positions and orientations based on which of the first selected one of the first plurality of possible positions and orientations and the second selected one of the second plurality of possible positions and orientations minimizes the cost function. In some examples, the undesirable relationship is selected from a group consisting of a collision between the first movable arm and the second movable arm, too close a proximity between the first movable arm and the second movable arm, and obstruction of a region of interest of the image capturing device by the first movable arm.

Consistent with some embodiments, a method of controlling movement in a medical system includes receiving one or more first configurations for a first movable arm of a computer-assisted surgical device, the first movable arm being coupled to a manipulatable device having a working end; receiving one or more second configurations for a second movable arm coupled to an image capturing device separate from the computer-assisted surgical device; receiving a first plurality of images of the working end from the image capturing device; determining, based on at least one of the first plurality of images, a position and an orientation of the working end in a common reference frame; determining, based on the first configurations, a first movable arm position and a first movable arm trajectory for the first movable arm in the common reference frame; determining, based on the second configurations, a second movable arm position and a second movable arm trajectory for the second movable arm in the common reference frame; based on the first movable arm position, the first movable arm trajectory, the second movable arm position, and the second movable arm trajectory, determining whether motion of the first movable arm, motion of the second movable arm, or motions of the first and second movable arms together will result in an undesirable relationship between the first and second movable arms; and sending a first movement command to the first movable arm or the second movable arm to avoid the undesirable relationship.

In some examples, the common reference frame is a reference frame of the image capturing device, and the method further includes determining the first movable arm position in the common reference frame further based on the position and the orientation of the working end in the common reference frame. In some examples, the common reference frame is a reference frame of the computer-assisted surgical device and the method further includes determining the second movable arm position in a reference frame of the image capturing device, determining the position and the orientation of the working end in the reference frame of the image capturing device, and transforming the second movable arm position and the position and orientation of the working end from the reference frame of the image capturing device to the common reference frame.

In some examples, the first plurality of images are a plurality of two-dimensional images from a image capturing device and the method further includes determining the position and the orientation of the working end from the two-dimensional images even when the working end of the manipulatable device is occluded by one or more objects disposed between the image capturing device and the working end of the manipulatable device. In some examples, the method further includes determining the first movement command so as to minimize a cost function.

Consistent with some embodiments, a movement control system includes a tracking system and a controller coupled to the tracking system. The controller includes one or more processors and memory coupled to the one or more processors. The controller is coupled to a computer-assisted surgical device having a first movable arm coupled to a manipulatable device having a working end. The controller is further coupled to a second movable arm coupled to an image capturing device separate from the computer-assisted surgical device. The controller is configured to receive first kinematic data for the first movable arm; receive second kinematic data for the second movable arm; receive first tracking data for the first movable arm from the tracking system; receive second tracking data for the second movable arm from the tracking system; determine, based on the first kinematic data and the first tracking data, a first location of the first movable arm; determine, based on the second kinematic data and the second tracking data, a second location of the second movable arm; send a first movement command to the second movable arm that directs the second movable arm to move into a first set-up position to capture images of at least a portion of the manipulatable device while maintaining a first safety margin between the first movable arm and the second movable arm, the first movement command being based on the first location and the second location; receive third kinematic data for the first movable arm; receive fourth kinematic data for the second movable arm; receive one or more first images from the image capturing device, the one or more first images capturing at least a portion of the manipulatable device; determine, based on the third kinematic data and the one or more first images, a third location of the first movable arm; determine, based on the fourth kinematic data and the one or more first images, a fourth location of the second movable arm; and send a second movement command to the second movable arm that directs the second movable arm to move into a second set-up position, different from the first set-up position, to capture images of a region of interest while maintaining a second safety margin between the first movable arm and the second movable arm, the second movement command being based on the third location and the fourth location.

In some examples, the controller is further configured to receive fifth kinematic data for the first movable arm; receive sixth kinematic data for the second movable arm; receive one or more second images from the image capturing device, the one or more second images capturing at least a portion of the working end; determine, based on the fifth kinematic data and the one or more second images, a fifth location of the first movable arm; determine, based on the sixth kinematic data and the one or more second images, a sixth location of the second movable arm; and send a third movement command to the second movable arm that directs the second movable arm to move into a third set-up position, different from the first set-up position and the second set-up position, to capture images of the working end while maintaining a third safety margin between the first movable arm and the second movable arm, the third movement command being based on the fifth location and the sixth location.

In some examples, the second safety margin is an order of magnitude smaller than the first safety margin. In some examples, maintaining the first safety margin keeps a separation between the first movable arm and the second movable arm of at least ten centimeters and maintaining the second safety margin keeps a separation between the first movable arm and the second movable arm of at least one centimeter. In some examples, the third safety margin is an order of magnitude smaller than the second safety margin. In some examples, maintaining the second safety margin keeps a separation between the first movable arm and the second movable arm of at least one centimeter and maintaining the third safety margin keeps a separation between the first movable arm and the second movable arm of at least one millimeter.

In some examples, the first images are two-dimensional images from a image capturing device and the controller is further configured to determine a position and an orientation of the manipulatable device from the two-dimensional images even when the manipulatable device is occluded by one or more objects disposed between the image capturing device and the working end of the manipulatable device. In some examples, the second images are two-dimensional images from a image capturing device and the controller is further configured to determine a position and an orientation of the working end from the two-dimensional images even when the working end of the manipulatable device is occluded by one or more objects disposed between the image capturing device and the working end of the manipulatable device. In some examples, the system further includes a viewer adapted to display one more second images received from the image capturing device and an input unit configured to receive information of the region of interest within the second images.

In some examples, the input unit includes a gaze tracking unit configured to track a gaze of a user on a display screen of the viewer and the gaze tracking unit includes an indicator operable by the user to indicate the region of interest by using a current gaze point of the user on the display screen. In some examples, the input unit includes a telestrator unit configured to receive one of the second of images and display the received one of the second images on a display screen of the telestrator and the telestrator unit includes a marker unit operable by a user to indicate the region of interest on the displayed one of the second images. In some examples, the system further includes a camera and the second images are captured by the camera. In some examples, the system further includes an ultrasound probe and the second images are captured by the ultrasound probe. In some examples, the first movement command minimizes a cost function.

In some examples, the second movable arm has redundant degrees of freedom so that for each controllable position and orientation of the image capturing device there are a plurality of possible positions and orientations for the second movable arm, the first movement command sent to the second movable arm directs the second movable arm to move to one of the plurality of possible positions and orientations that maintain the first safety margin, the second movement command sent to the second movable arm directs the second movable arm to move to one of the plurality of possible positions and orientations that maintain the second safety margin, and the third movement command sent to the second movable arm directs the second movable arm to move to one of the plurality of possible positions and orientations that maintain the third safety margin.

Consistent with some embodiments, a method of controlling movement in a medical system includes receiving first kinematic data for a first movable arm of a computer-assisted surgical device, the first movable arm being coupled to a manipulatable device having a working end; receiving second kinematic data for a second movable arm coupled to an image capturing device separate from the computer-assisted surgical device; receiving first tracking data for the first movable arm from a tracking system; receiving second tracking data for the second movable arm from the tracking system; determining, based on the first kinematic data and the first tracking data, a first location of the first movable arm; determining, based on the second kinematic data and the second tracking data, a second location of the second movable arm; sending a first movement command to the second movable arm that directs the second movable arm to move into a first set-up position to capture images of at least a portion of the manipulatable device while maintaining a first safety margin between the first movable arm and the second movable arm, the first movement command being based on the first location and the second location; receiving third kinematic data for the first movable arm; receiving fourth kinematic data for the second movable arm; receiving one or more first images from the image capturing device, the one or more first images capturing at least a portion of the manipulatable device; determining, based on the third kinematic data and the one or more first images, a third location of the first movable arm; determining, based on the fourth kinematic data and the one or more first images, a fourth location of the second movable arm; and sending a second movement command to the second movable arm that directs the second movable arm to move into a second set-up position, different from the first set-up position, to capture images of a region of interest while maintaining a second safety margin between the first movable arm and the second movable arm, the second movement command being based on the third location and the fourth location.

In some examples, the method further includes receiving fifth kinematic data for the first movable arm; receiving sixth kinematic data for the second movable arm; receiving one or more second images from the image capturing device, the one or more second images capturing at least a portion of the working end; determining, based on the fifth kinematic data and the one or more second images, a fifth location of the first movable arm; determining, based on the sixth kinematic data and the one or more second images, a sixth location of the second movable arm; and sending a third movement command to the second movable arm that directs the second movable arm to move into a third set-up position, different from the first set-up position and the second set-up position, to capture images of the working end while maintaining a third safety margin between the first movable arm and the second movable arm, the third movement command being based on the fifth location and the sixth location.

In some examples, the method further includes determining the third movement command so as to minimize a cost function. In some examples, the first images are two-dimensional images from a image capturing device and the method further includes determining a position and an orientation of the manipulatable device from the two-dimensional images even when the manipulatable device is occluded by one or more objects disposed between the image capturing device and the working end of the manipulatable device. In some examples, the second images are two-dimensional images from a image capturing device and the method further includes determining a position and an orientation of the working end from the two-dimensional images even when the working end of the manipulatable device is occluded by one or more objects disposed between the image capturing device and the working end of the manipulatable device.

Consistent with some embodiments, a robotic system includes a first robot arm holding a manipulatable device having a working end and a controller configured to control movement of at least one of the first robot arm and a second robot arm while avoiding a collision between the first and second robot arms. The second robot arm holds an image capturing device for capturing a plurality of images of the working end of the manipulatable device from which a three-dimensional computer model of the working end of the manipulatable device is generatable. The controller is configured to avoid the collision between the first and second robot arms by determining a position and an orientation of the working end of the manipulatable device relative to a reference frame of the image capturing device by using at least one image of the plurality of images of the working end of the manipulatable device, wherein the reference frame of the image capturing device corresponds to a perspective of the captured images; by determining a configuration and position of one of the first and second robot arms relative to a common reference frame by using the determined position and orientation of the working end of the manipulatable device relative to the reference frame of the image capturing device; and by determining a configuration and position of the other of the first and second robot arms relative to the common reference frame by using joint position information received for the other of the first and second robot arms; by determining an imminent collision between the first and second robot arms using the determined configurations and positions of the first and second robot arms relative to the common reference frame; and by commanding an action to be taken by one of the first and second robot arms to avoid the imminent collision.

In some examples, the image capturing device includes a tomographic image capturing device for capturing a plurality of two-dimensional images from which the working end of the manipulatable device is discernible even when the working end of the manipulatable device is occluded by one or more objects disposed between the image capturing device and the working end of the manipulatable device. In some examples, the controller is configured to determine the configuration and position of the first robot arm relative to the reference frame of the image capturing device by using information of the construction and geometry of the first robot arm and the determined position and orientation of the working end of the manipulatable device relative to the reference frame of the image capturing device.

In some examples, the controller is configured to determine the configuration and position of the second robot arm relative to a reference frame of the manipulatable device by using a transform to translate points in the reference frame of the image capturing device to the reference frame of the manipulatable device. The transform has been determined by using the determined position and orientation of the working end of the manipulatable device relative to the reference frame of the image capturing device. The reference frame of the manipulatable device is the common reference frame. In some examples, the system further includes a viewer adapted to display images derived from captured images of a work space of the working end of the manipulatable device and an input unit configured to receive information of a user specified region of interest within the images being displayed on the viewer. The controller is configured to command and control movement of the second robot arm so that the image capturing device captures images of the user specified region of interest in the plurality of images of the working end of the manipulatable device.

In some examples, the input unit includes a gaze tracking unit configured to track a gaze of a user on a display screen of the viewer. The gaze tracking unit includes an indicator operable by the user to indicate the region of interest by using a current gaze point of the user on the display screen. In some examples, the input unit includes a telestrator unit configured to receive an image being displayed on the viewer and display the received image on a display screen of the telestrator. The telestrator unit includes a marker unit operable by a user to indicate the region of interest on the image being displayed on the display screen of the telestrator unit.

In some examples, the system further includes a camera and the captured images of the work space of the working end of the manipulatable device are captured by the camera. In some examples, the system further includes an ultrasound probe and the captured images of the work space of the working end of the manipulatable device are captured by the ultrasound probe. In some examples, the controller is associated with the first robot arm to control movement of the first robot arm while avoiding a collision with the second robot arm and a reference frame of the manipulatable device is the common reference frame. In some examples, the controller is associated with the second robot arm to control movement of the second robot arm while avoiding a collision with the first robot arm, and the reference frame of the image capturing device is the common reference frame.

In some examples, the first robot arm includes a first plurality of joints and a first plurality of links that are coupled together to provide redundant degrees of freedom movement of the first robot arm so that for each controllable position and orientation of the working end of the manipulatable device there are a plurality of possible configurations for the first robot arm. The controller is configured to control movement of the first robot arm by commanding the first robot arm to be configured in one of the plurality of possible configurations for the first robot arm according to a desired position and orientation of the working end of the manipulatable device and according to a secondary constraint for avoiding a collision between the first and second robot arms.

In some examples, the second robot arm includes a second plurality of joints and a second plurality of links that are coupled together to provide redundant degrees of freedom movement of the second robot arm so that for each controllable position and orientation of the image capturing device there are a plurality of possible configurations for the second robot arm. The controller is configured to control movement of the second robot arm by commanding the second robot arm to be configured in one of the plurality of possible configurations for the second robot arm according to a desired position and orientation of the image capturing device and according to a secondary constraint for avoiding a collision between the first and second robot arms.

In some examples, the first robot arm includes a first plurality of joints and a first plurality of links that are coupled together to provide redundant degrees of freedom movement of the first robot arm so that for each controllable position and orientation of the working end of the manipulatable device there are a plurality of possible configurations for the first robot arm. The second robot arm includes a second plurality of joints and a second plurality of links that are coupled together to provide redundant degrees of freedom movement of the second robot arm so that for each controllable position and orientation of the image capturing device there are a plurality of possible configurations for the second robot arm. The controller is configured to control movement of one of the first and second robot arms to be configured in one of its plurality of possible configurations to avoid a collision with the other one of the first and second robot arms.

In some examples, the controller is configured to determine which one of the first and second robot arms is to be configured in one of its plurality of possible configurations to avoid a collision with the other one of the first and second robot arms by processing differences between current configurations of the first and second robot arms and their respective pluralities of possible configurations to minimize a cost function. In some examples, the controller is configured to determine which one of the first and second robot arms is to be configured in one of its plurality of possible configurations to avoid a collision with the other one of the first and second robot arms by processing required joint movements of the first and second robotic systems to move from their current configurations to others of their respective pluralities of possible configurations to minimize a cost function.

Consistent with some embodiments is a method for avoiding collisions between first and second robot arms. The first robot arm holds a manipulatable device having a working end. The second robot arm holds an image capturing device for capturing a plurality of images of the working end of the manipulatable device from which a three-dimensional computer model of the working end of the manipulatable device is generatable. The method includes determining a position and an orientation of the working end of the manipulatable device relative to a reference frame of the image capturing device by using at least one image of the plurality of images of the working end of the manipulatable device, wherein the reference frame of the image capturing device corresponds to a perspective of the captured images; determining a configuration and position of one of the first and second robot arms relative to a common reference frame by using the determined position and orientation of the working end of the manipulatable device relative to the reference frame of the image capturing device; determining a configuration and position of the other of the first and second robot arms relative to the common reference frame by using joint position information received for the other of the first and second robot arms; determining an imminent collision between the first and second robot arms using the determined configurations and positions of the first and second robot arms relative to the common reference frame; and commanding an action to be taken by one of the first and second robot arms to avoid the imminent collision.

Consistent with some embodiments, a robotic system includes a first robot arm that is holding a manipulatable device having a working end and a processor programmed to register the first robot arm to a second robot arm that is holding an image capturing device. The processor performs the registration by performing a low accuracy registration of the first and second robot arms at initial positions of the first and second robot arms using external tracking data and kinematics data of at least one of the first and second robot arms; performing a mid accuracy registration of the first and second robot arms relative to a first setup position using at least one image captured by the image capturing device of at least a part of the first robot arm and kinematics data of at least one of the first and second robot arms, wherein the first setup position includes a first safety margin indicative of the low accuracy registration; and performing a high accuracy registration of the first and second robot arms relative to a second setup position using at least one image captured by the image capturing device of the working end of the manipulatable device and kinematics data of at least one of the first and second robot arms, wherein the second setup position includes a second safety margin indicative of the mid accuracy registration.

Consistent with some embodiments is a method implemented by a processor for registering first and second robot arms. The first robot arm holds a manipulatable device having a working end. The second robot arm holds an image capturing device. The method includes performing a low accuracy registration of the first and second robot arms at initial positions of the first and second robot arms using external tracking data and kinematics data of at least one of the first and second robot arms, performing a mid accuracy registration of the first and second robot arms relative to a first setup position using at least one image captured by the image capturing device of at least a part of the first robot arm and kinematics data of at least one of the first and second robot arms, wherein the first setup position includes a first safety margin indicative of the low accuracy registration, and performing a high accuracy registration of the first and second robot arms relative to a second setup position using at least one image captured by the image capturing device of the working end of the manipulatable device and kinematics data of at least one of the first and second robot arms, wherein the second setup position includes a second safety margin indicative of the mid accuracy registration.

Additional objects, features and advantages of the various aspects of the present invention will become apparent from the following description of its preferred embodiment, whose description should be taken in conjunction with the accompanying drawings.

DETAILED DESCRIPTION

Figure 1:
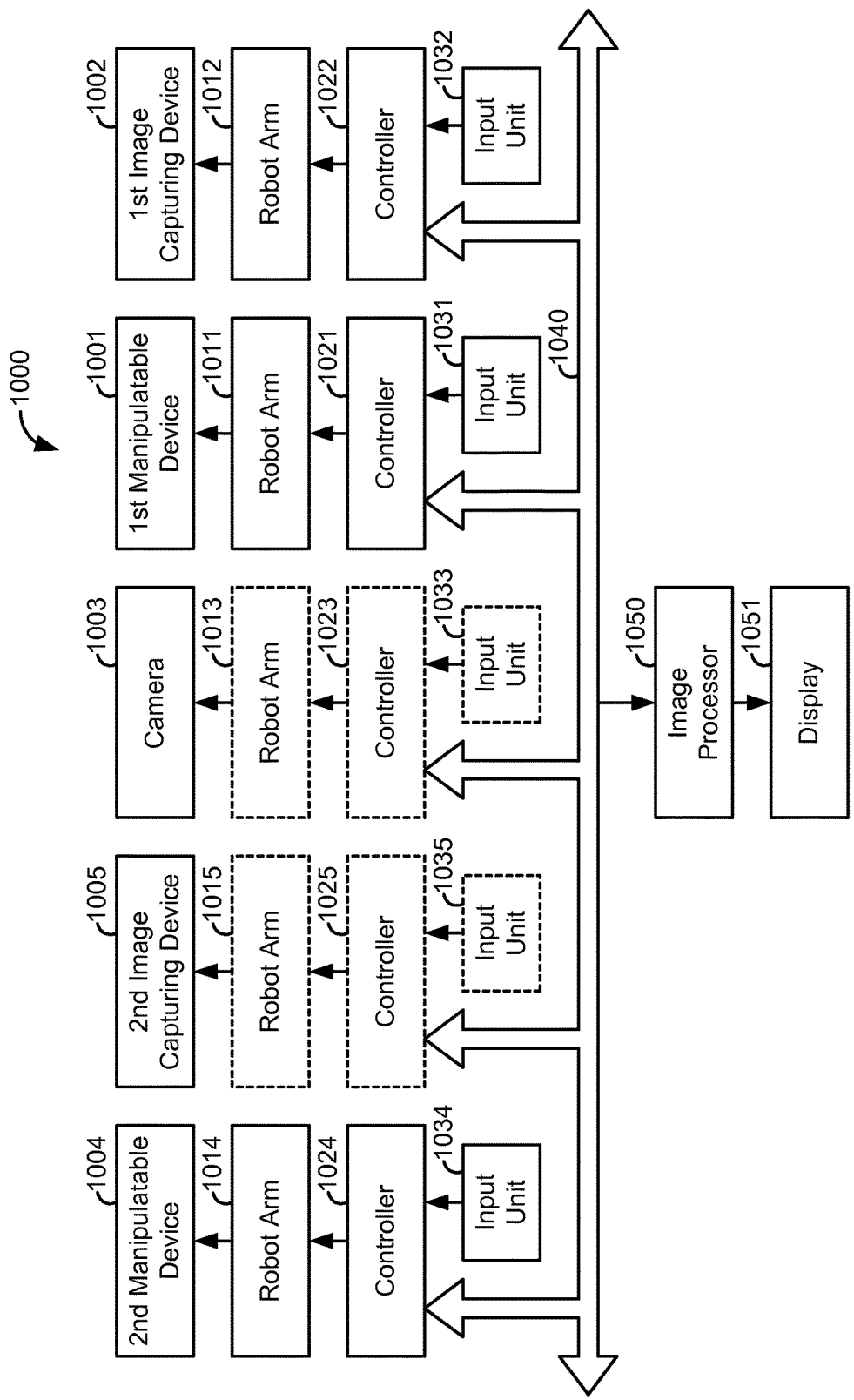
FIG. 1 illustrates a block diagram of a robotic system utilizing aspects of the present invention.
Figure 2:
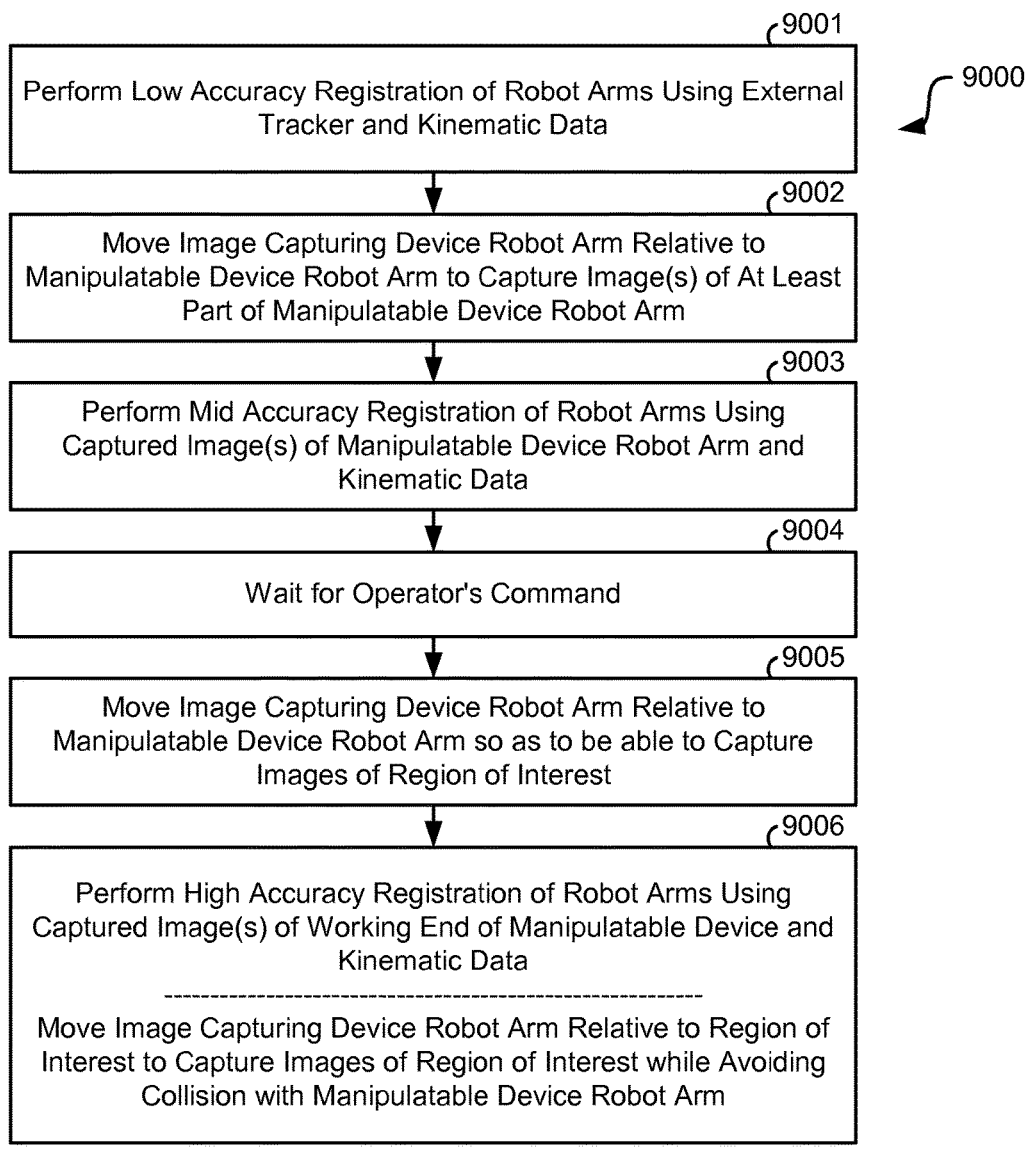
FIG. 2 illustrates a flow diagram of a method, implemented in a robotic system utilizing aspects of the present invention, for performing multi-accuracy registration of an image capturing device robot arm and a manipulatable device robot arm as the image capturing device robot arm moves relative to the manipulatable device robot arm.
Figure 3:
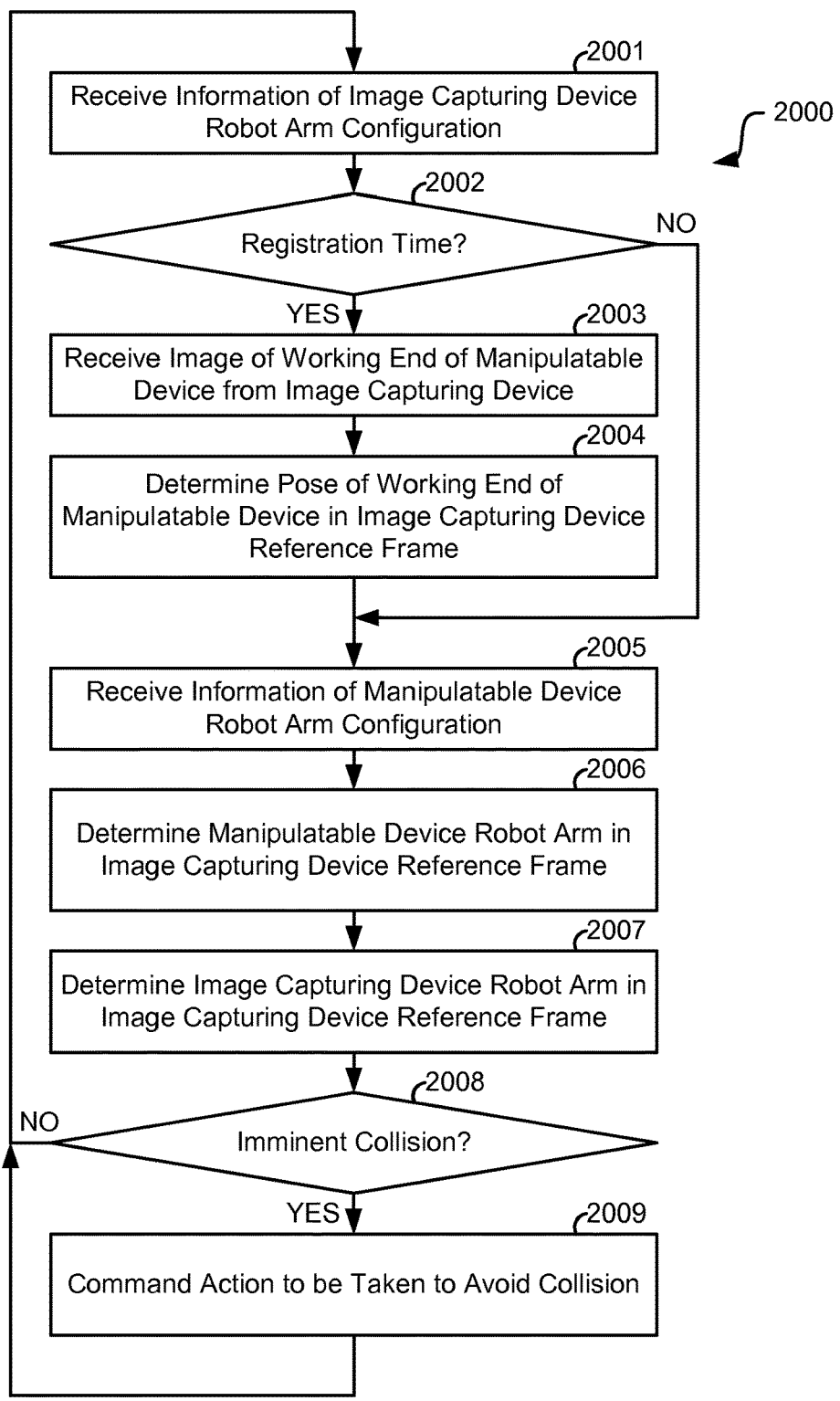
FIG. 3 illustrates a flow diagram of a method, implemented in a robotic system utilizing aspects of the present invention, for automatically avoiding a collision between independently operated robot arms from the perspective of an image capturing device reference frame.
Figure 4:
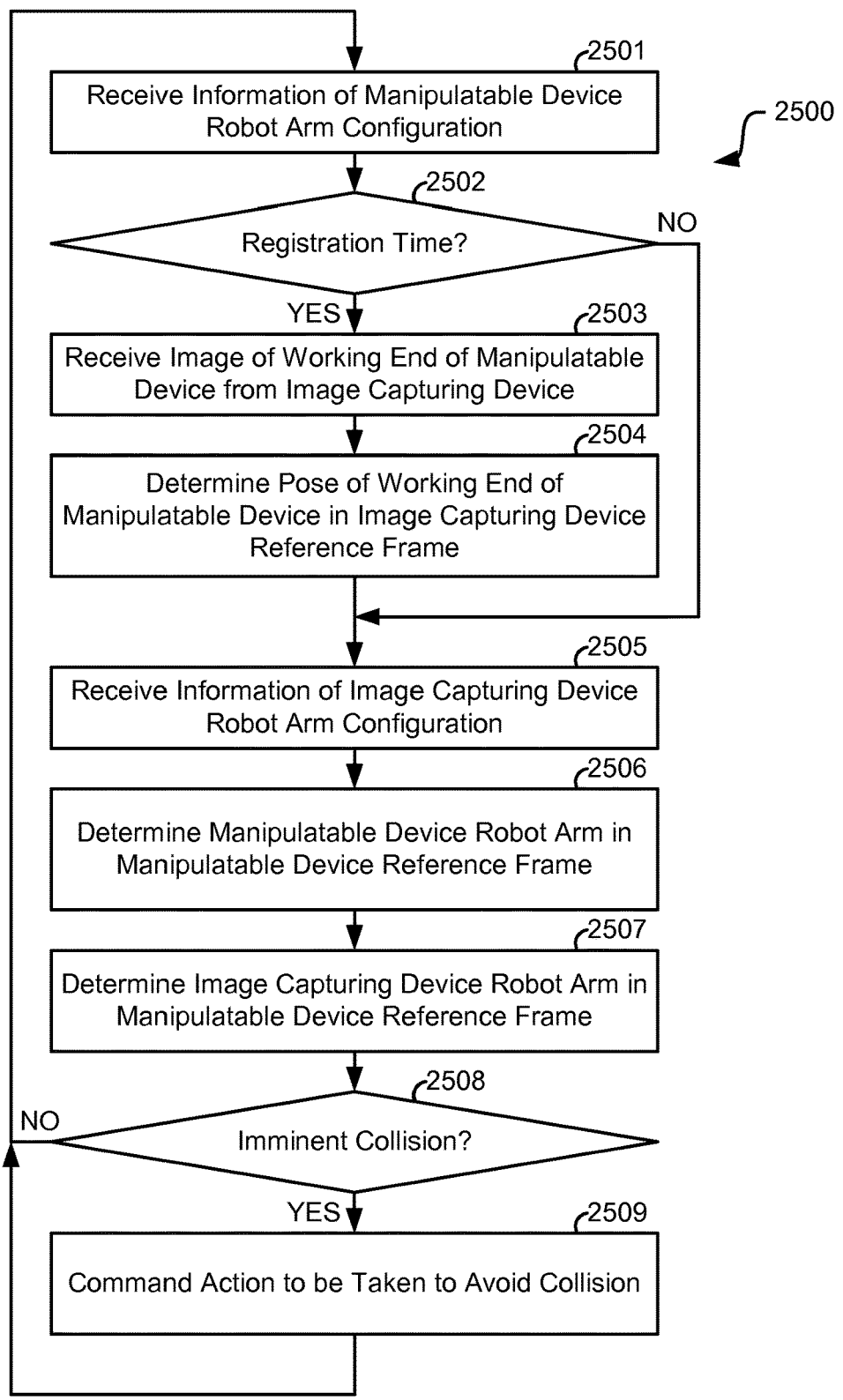
FIG. 4 illustrates a flow diagram of the method, implemented in a robotic system utilizing aspects of the present invention, for automatically avoiding a collision between independently operated robot arms from the perspective of a manipulatable device reference frame.
Figure 5:
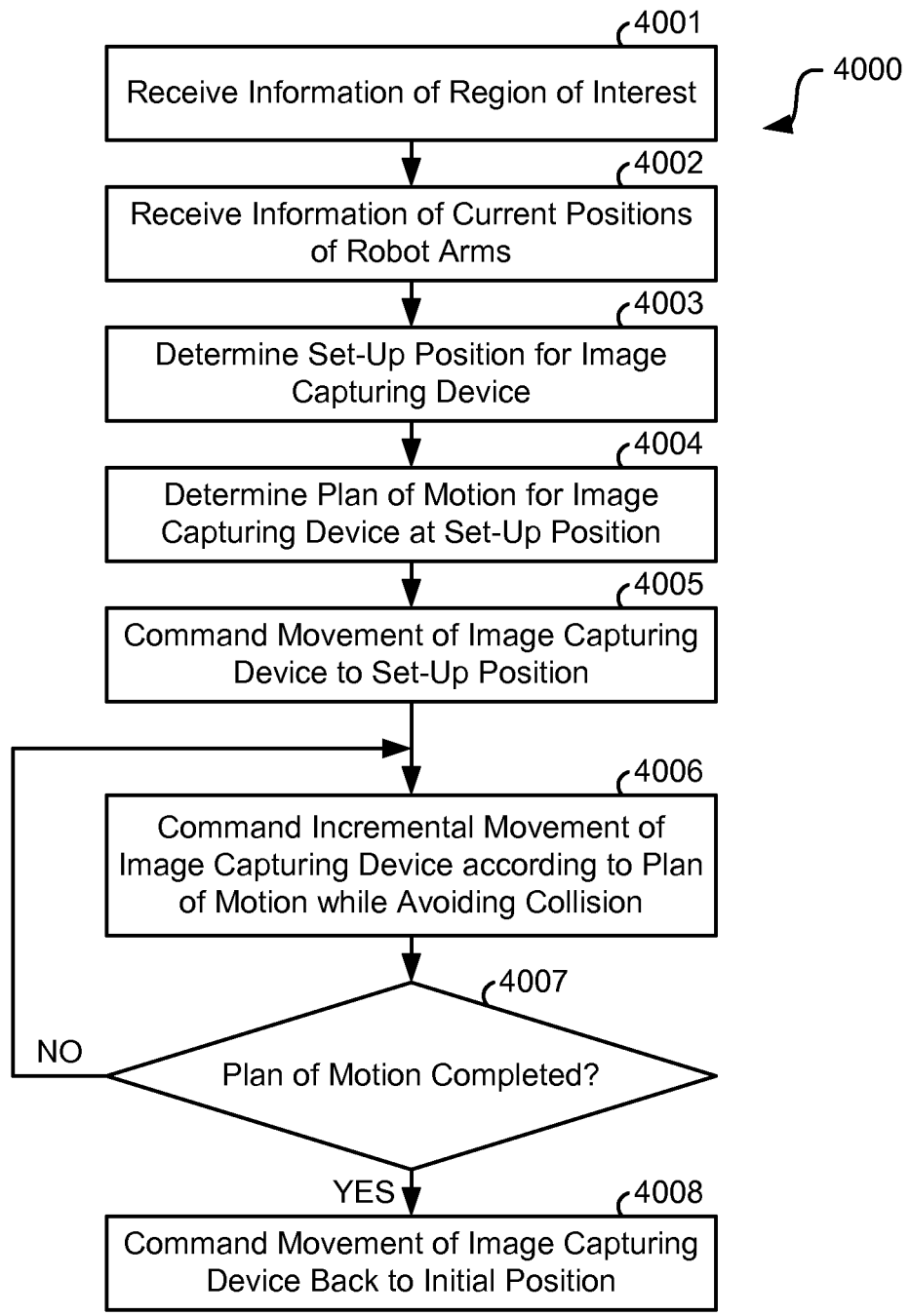
FIG. 5 illustrates a flow diagram of a method, implemented in a robotic system utilizing aspects of the present invention, for controlling an image capturing device robot arm so that its image capturing device captures images of a user selected region of interest while avoiding a collision with another robot arm.
Figure 6:
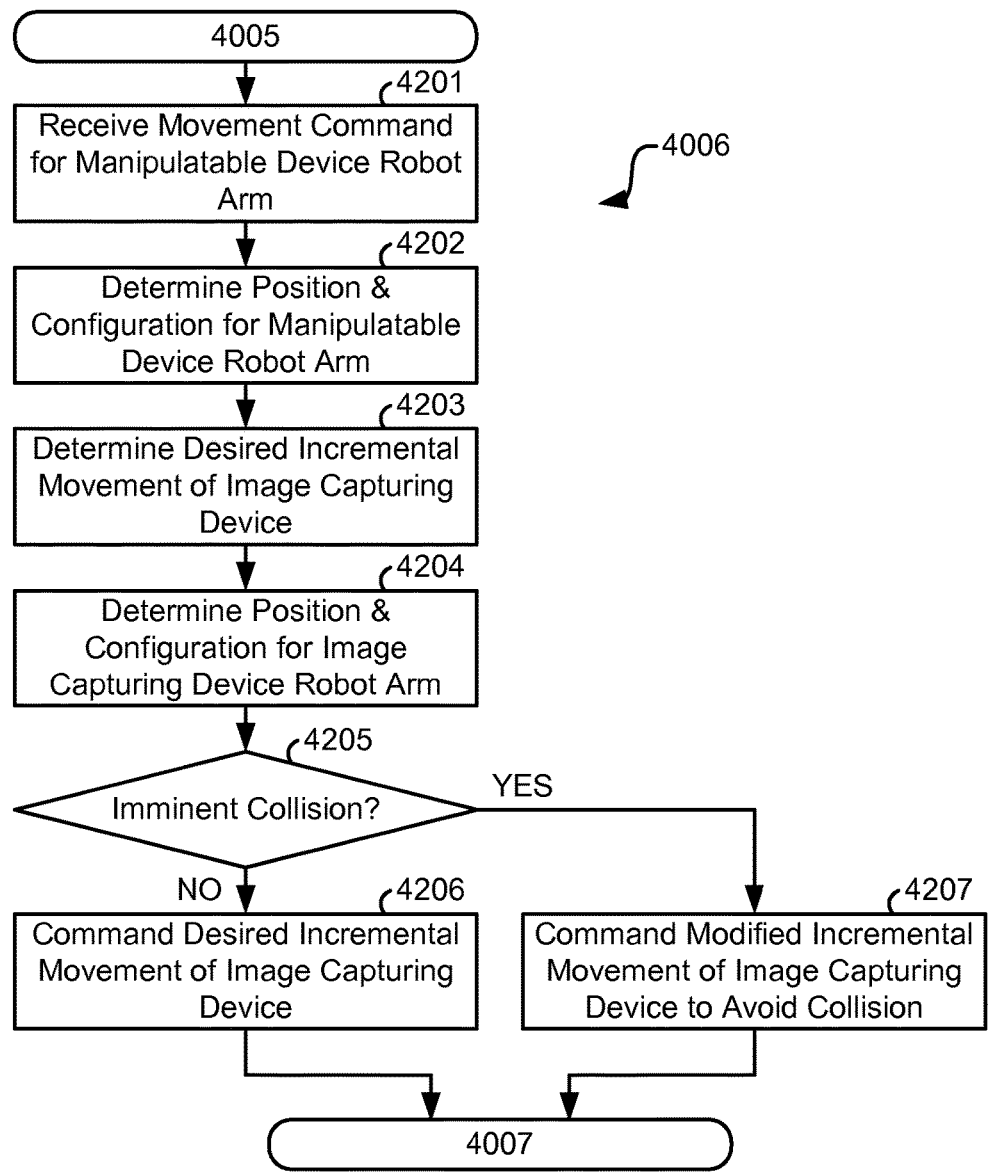
FIG. 6 illustrates a flow diagram of a method, implemented in a robotic system utilizing aspects of the present invention, for controlling movement of an image capturing device robot arm according to a plan of motion while avoiding a collision with another robot arm.
Figure 7:
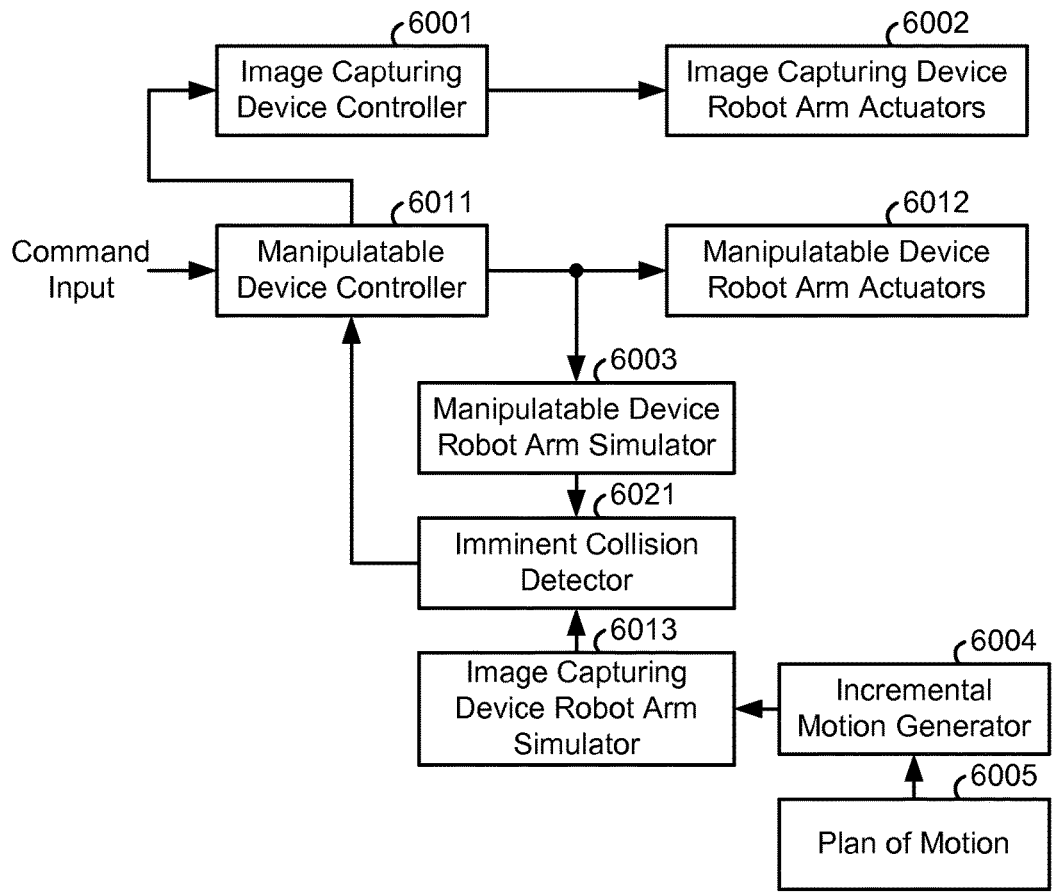
FIG. 7 illustrates a block diagram of a portion of a robotic system utilizing aspects of the present invention, which is used for collision avoidance of two robot arms operating in a coupled-control mode.
Figure 13:
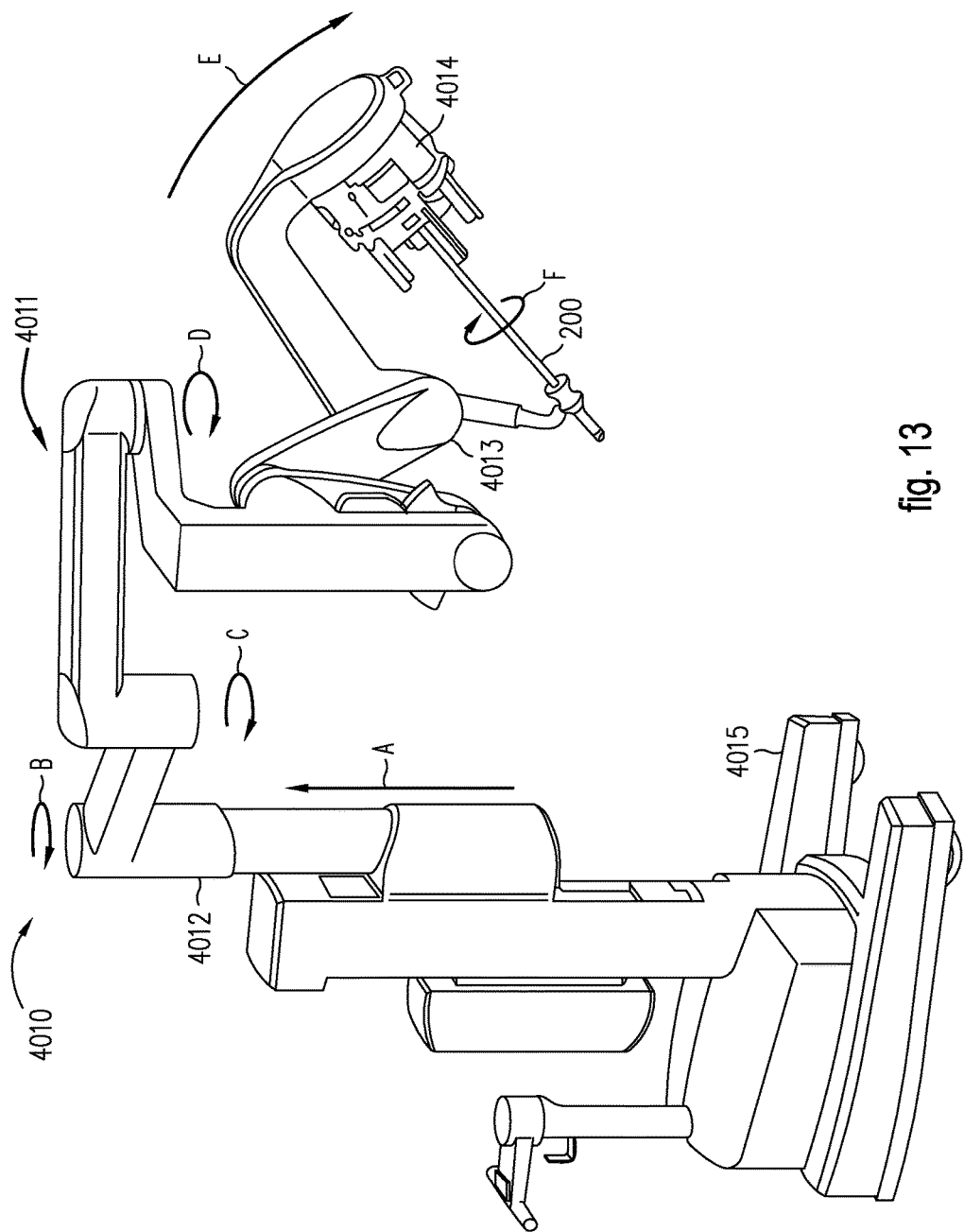
FIG. 13 illustrates a perspective view of a Patient-Side Cart for a single aperture medical robotic system in which aspects of the present invention are usable.
Figure 14:
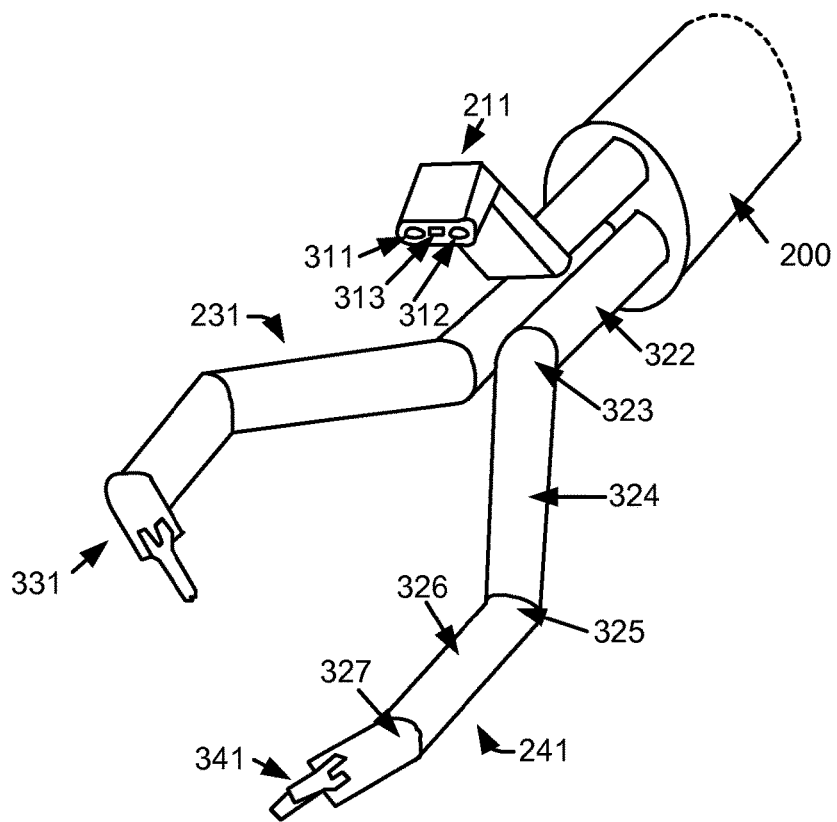
FIG. 14 illustrates a perspective view of a distal end of an entry guide with articulated instruments extending out of it as used in a single aperture medical robotic system in which aspects of the present invention are usable.
Figure 15:
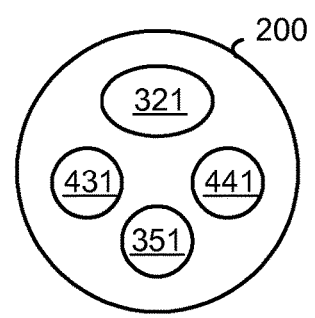
FIG. 15 illustrates a cross-sectional view of an entry guide as used in a single aperture medical robotic system in which aspects of the present invention are usable.

FIG. 1 illustrates, as an example, a block diagram of various components of a robotic or computer-assisted system 1000 in which methods 2000, 2500, and 4000 are implemented for automatically avoiding a collision between two or more robot or movable arms. FIG. 2 describes a multi-step approach to registration of robot or movable arms. FIGS. 3, 4 are provided to describe the methods 2000, 2500 which are generally applicable to independently operated robot or movable arms. FIGS. 5-7 are provided to describe the method 4000 which is generally applicable to controlling movement of an image capturing device robot or movable arm through a controller which is controlling a manipulatable device robot or movable arm. Examples of the robotic system 1000 in which the methods 2000, 2500, and 4000 may be used are described in reference to FIGS. 8-15. FIGS. 8-12 are provided to describe a robotic or computer-assisted system 3000 using a Patient-Side Cart 3010 with multiple robot or movable arms which is suitable for performing procedures with multiple apertures for entry to a work site. FIGS. 13-15 are provided to describe an alternative Patient-Side Cart 4010 for the robotic system 3000, in which the Patient-Side Cart 4010 has a single robot or movable arm which is suitable for performing procedures with a single aperture for entry to a work site.

Before describing details of the methods 2000, 2500, 4000 as illustrated in FIGS. 1-7, the robotic or computer-assisted system 3000 will first be described to provide context and additional details on implementations of the robotic or computer-assisted system 1000. Although a medical robotic or computer-assisted surgical system is described herein as an example of the robotic or computer-assisted system 1000, it is to be appreciated that the various aspects of the invention as claimed herein are not to be limited to such types of robotic or computer-assisted systems.

Figure 8:
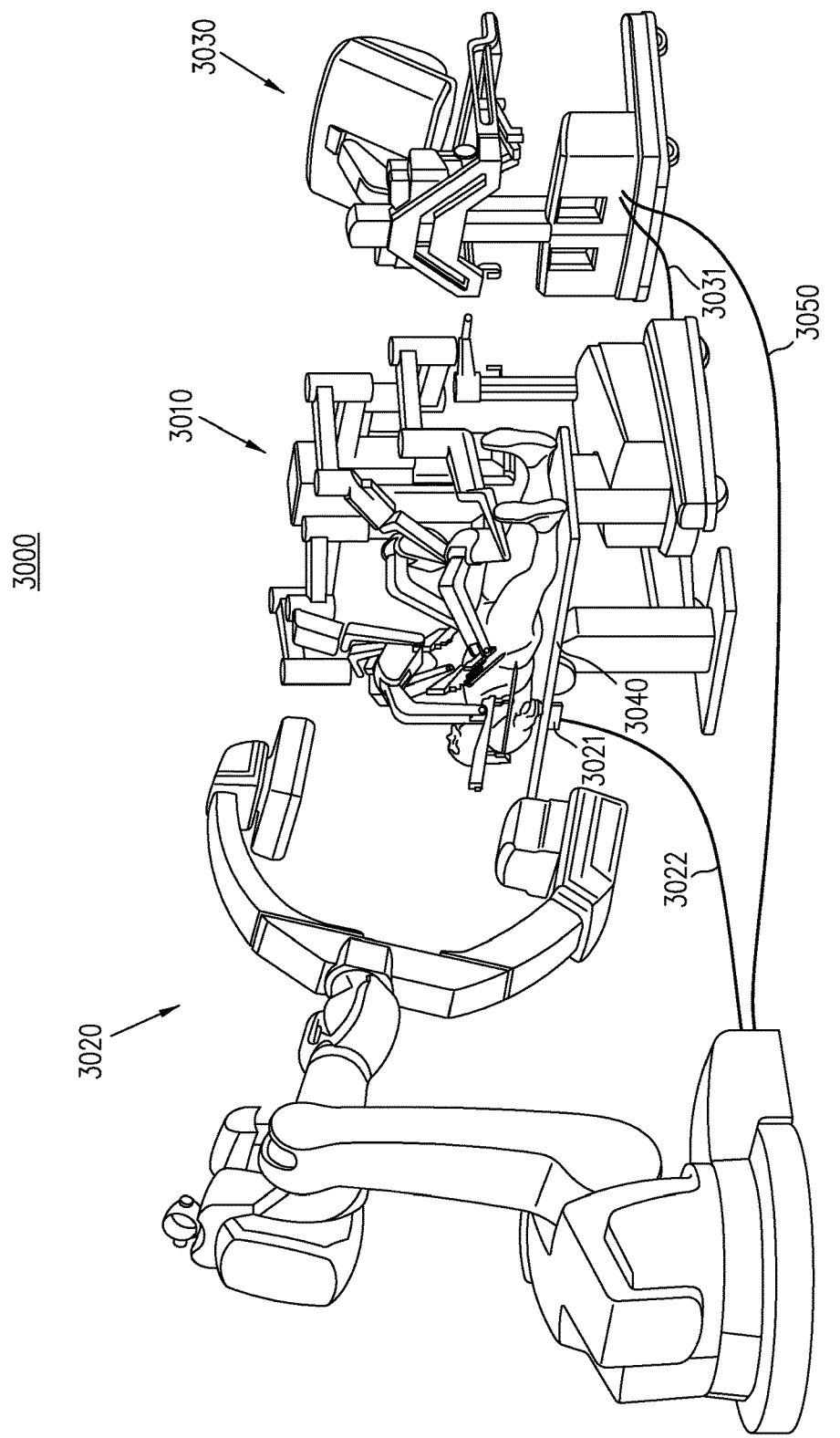
FIG. 8 illustrates a perspective view of an operating room employing a multiple aperture medical robotic system in which aspects of the present invention are usable.

Referring to FIG. 8, a perspective view of an operating room is illustrated in which a medical robotic system 3000 is provided for a Surgeon to perform a medical procedure on a Patient. The medical robotic system in this case is a Minimally Invasive Robotic Surgical (MIRS) system including a Patient-Side Cart 3010, an Image Capturing System 3020, and a Console 3030.

Figure 9:
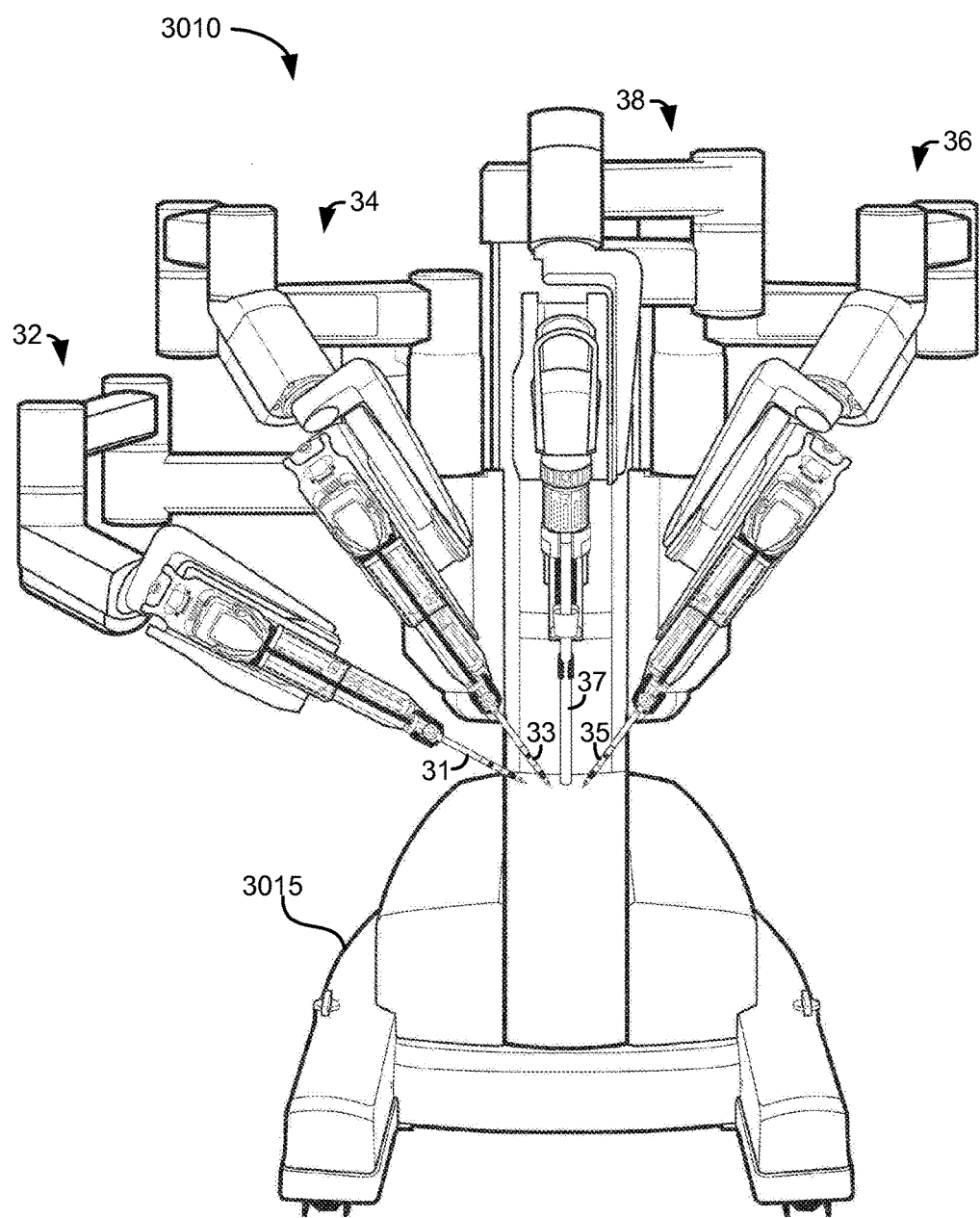
FIG. 9 illustrates a front view of a Patient-Side Cart for a multiple aperture medical robotic system in which aspects of the present invention are usable.

The Patient-Side Cart 3010, as described in detail in reference to FIG. 9, has a plurality of robot arms for holding and manipulating a plurality of devices such as instruments and at least one endoscope. When using the Patient-Side Cart 3010, each of the devices being held by the plurality of robot or movable arms is introduced through its own entry aperture into a Patient.

Figure 11:
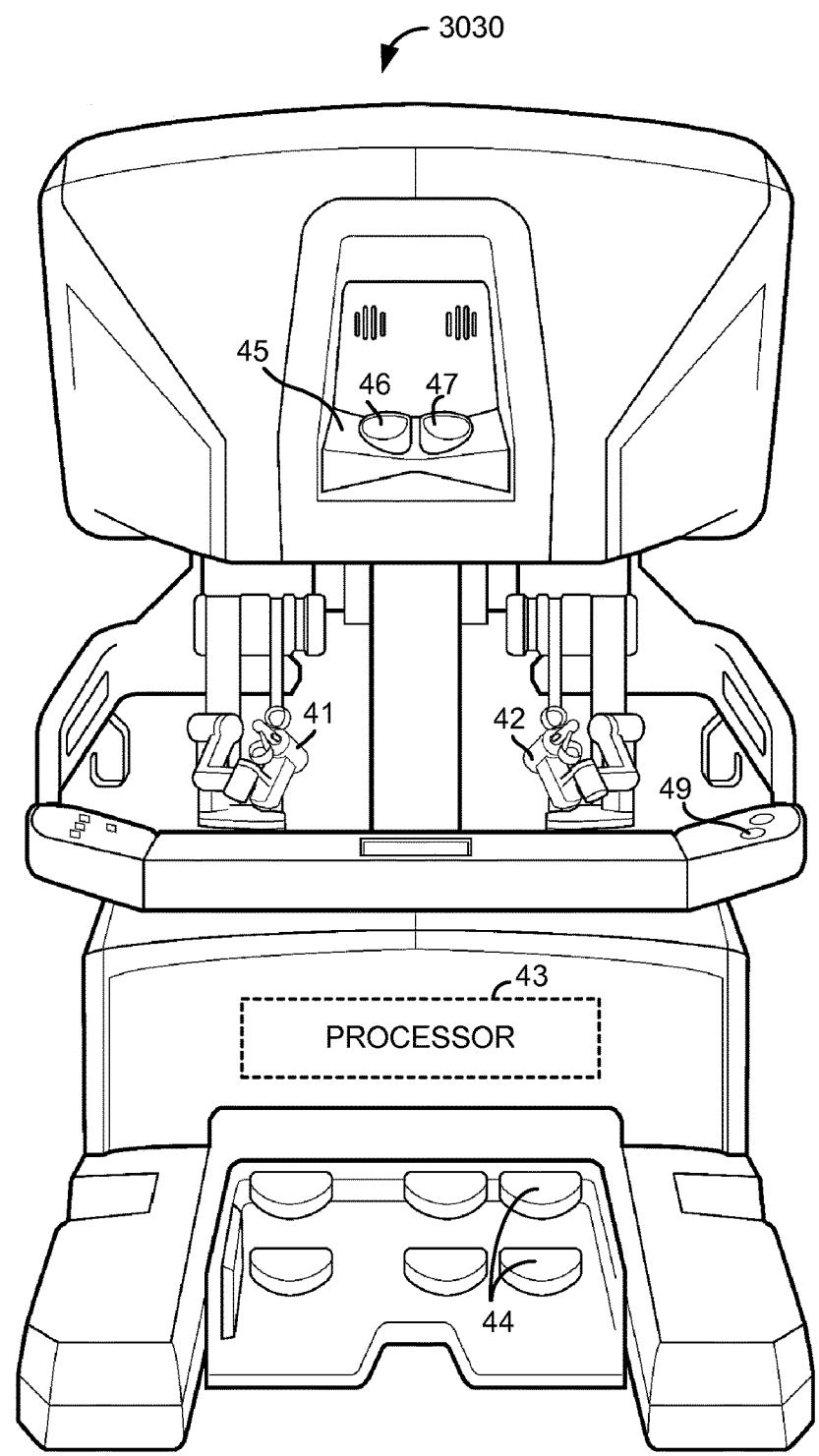
FIG. 11 illustrates a front view of a console of a robotic system utilizing aspects of the present invention.

The Console 3030, as described in detail in reference to FIG. 11, includes input devices for commanding movement of associated ones of the plurality of robot arms of the Patient-Side Cart 3010 and the operation of their respectively held devices. The Console 3030 and the Patient-Side Cart 3010 communicate through a cable 3031.

Figure 12:
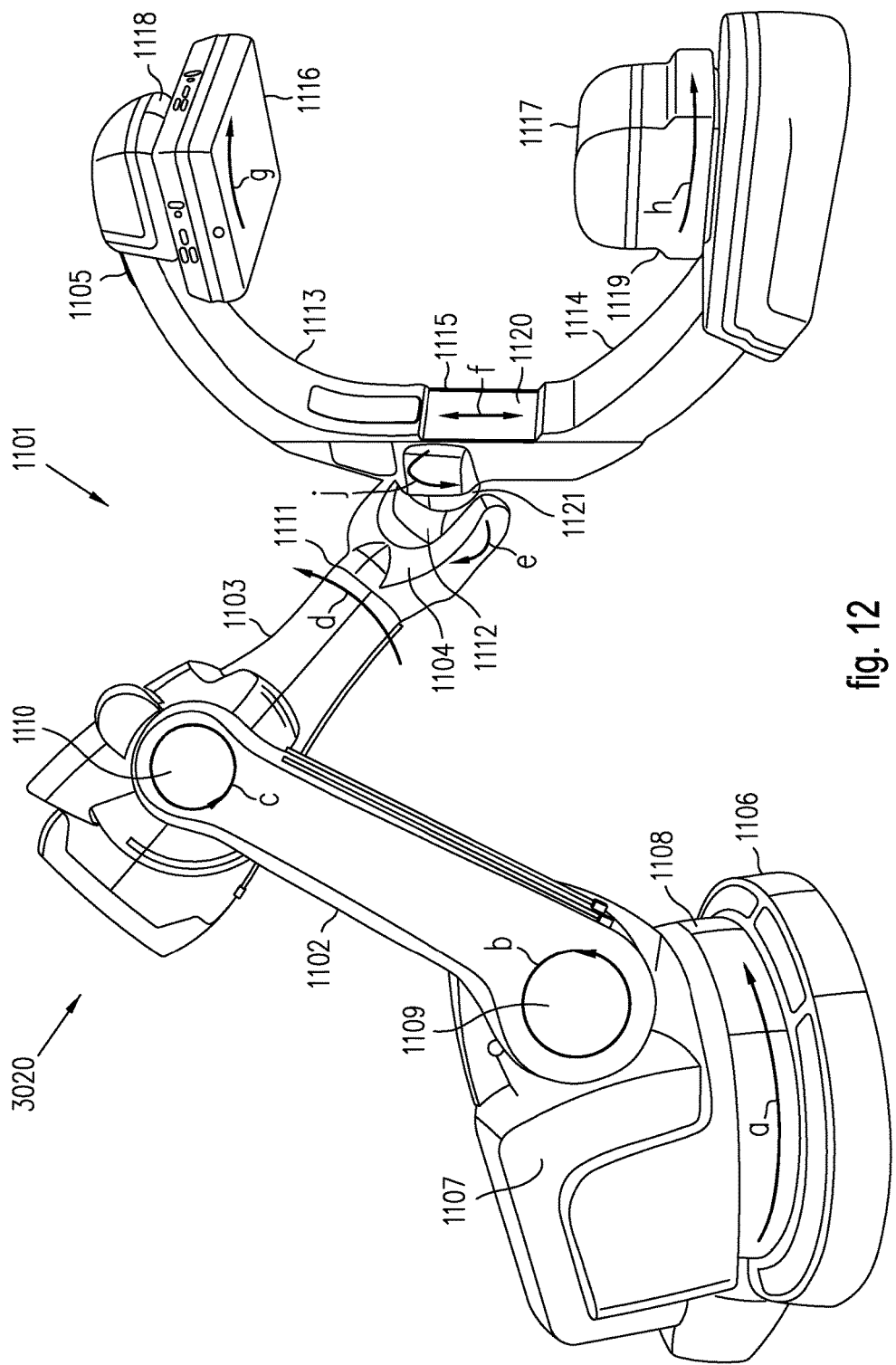
FIG. 12 illustrates a perspective view of an image capturing system usable in a robotic system utilizing aspects of the present invention.

The Image Capturing System 3020, as described in detail in reference to FIG. 12, captures a plurality of images, such as a series of two-dimensional image projections, of one or more objects within a specified region of interest at a work site in the Patient. The plurality of images may then be used to generate a three-dimensional computer model of the one or more objects without requiring prior knowledge of the three-dimensional shapes of the one or more objects, in a conventional manner such as used in computed tomography.

A control unit 3021 may be provided beneath or to the side of an articulated operating table 3040, so that an Assistant may manually control movement of an image capturing device of the Image Capturing System 3020 using a joy stick or other control input provided on the control unit 3021. The control unit 3021 and the Image Capturing System 3020 communicate through cable 3022 or using wireless technology. Alternatively, the control unit 3021 may be provided at another location and communicate with the Image Capturing System 3020 as a wired or wireless mobile entity. The control unit 3021 may include at least one processing unit and memory. In some examples, the processing unit may control operation and/or execution of hardware and/or software in control unit 3021. The processing unit may include one or more central processing units (CPUs), multi-core processors, microprocessors, microcontrollers, digital signal processors, field programmable gate arrays (FPGAs), custom processors/application specific integrated circuits (ASICs), and/or the like. The memory may be used to store one or more software and/or firmware applications as well as various data structures to be used by control unit 3021. The memory may also include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Alternatively, movement of the image capturing device of the Image Capturing System 3020 may be controlled by the Surgeon operating an associated one of the input devices of the Console 3030 according to aspects of the present invention. Alternatively, movement of the image capturing device of the Image Capturing System 3020 may be controlled automatically by a processor of the Console 3030 so that the image capturing device automatically captures a plurality of images of a user specified region of interest in the work site while avoiding a collision with the robot arms of the Patient-Side Cart 3010 according to aspects of the present invention. The Console 3030 and the Image Capturing System 3020 communicate through cable 3050.

FIG. 9 illustrates, as an example, a front view of the Patient-Side Cart 3010. In a typical application, robot arms 34, 36 hold instruments 33, 35 and robot arm 38 holds stereo endoscope 37. The fourth robot arm 32 is available so that another instrument 31 may be introduced at the work site along with the instruments 33, 35 and endoscope 37. Alternatively, the fourth robot arm 32 may be used for introducing a second endoscope or another image capturing device, such as an ultrasound transducer, to the work site.

Each of the robot or movable arms is conventionally formed of links which are coupled together and manipulated through actuatable joints. Each of the robot arms includes a setup arm and a device manipulator. The setup arm positions its held device so that a pivot point occurs at its entry aperture into the Patient. The device manipulator may then manipulate its held device so that it may be pivoted about the pivot point, inserted into and retracted out of the entry aperture, and rotated about its shaft axis. In this example, the robot arms are mounted on a movable base 3015 of the Patient-Side Cart 3010. Alternatively, the robot arms may be attached to sliders on a side of the operating table, to sliders on a wall or to sliders on the ceiling of the operating room.

Figure 10:
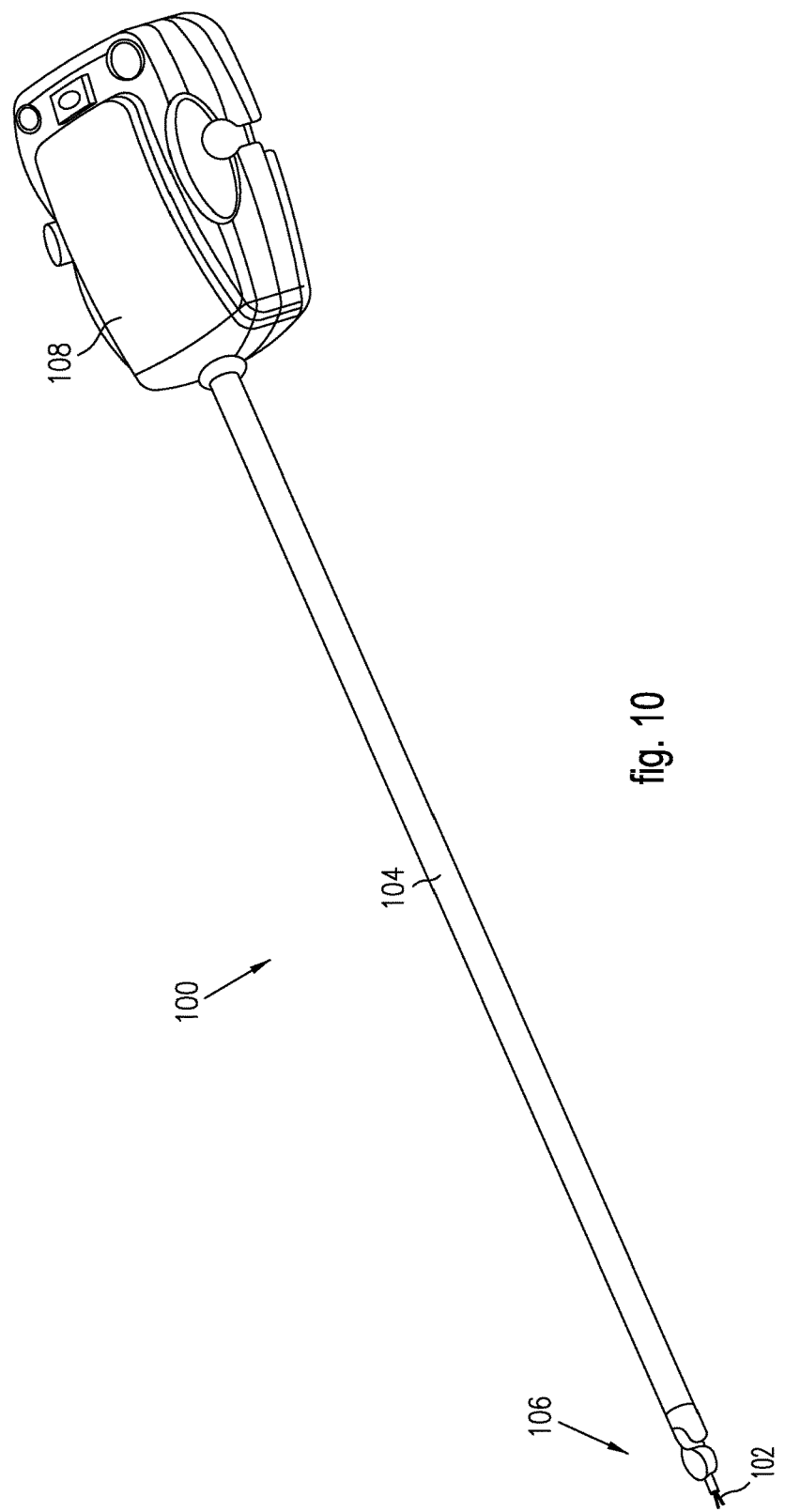
FIG. 10 illustrates a perspective view of an instrument usable in a multiple aperture medical robotic system in which aspects of the present invention are usable.

FIG. 10 illustrates, as an example, an instrument 100 that may be used for either instrument 33, 35 or 31. The instrument 100 comprises an interface housing 108, a shaft 104, a working end 102, and a wrist mechanism 106 which includes one or more wrist joints. The interface housing 108 is removably attached to a robot arm so as to be mechanically coupled to actuators (such as motors) in the instrument manipulator of the attached robot arm. Cables or rods, that are coupled to the actuators of the instrument manipulator and extend through the shaft 104 from the interface housing 108 to the one or more wrist joints of the wrist mechanism 106 and to the jaws of the instrument's end effector 102, actuate the wrist joints and jaws in a conventional manner. The instrument manipulator may also manipulate the instrument in pitch and yaw angular rotations about its pivot point at the entry aperture, manipulate the instrument in a roll angular rotation about the instrument's shaft axis, and insert and retract the instrument along a rail on the robot arm as commanded by the processor 43.

FIG. 11 illustrates, as an example, a front view of the Console 3030. The Console 3030 has left and right input devices 41, 42 which the user may grasp respectively with his/her left and right hands to manipulate associated devices being held by the plurality of robot or movable arms of the Patient-Side Cart 3010 in preferably six degrees-of-freedom ("DOF"). Foot pedals 44 with toe and heel controls are provided on the Console 3030 so the user may control movement and/or actuation of devices associated with the foot pedals. A processor 43 is provided in the Console for control and other purposes. A stereo vision display 45 is also provided in the Console so that the user may view the work site in stereo vision from images captured by the stereoscopic camera of the endoscope 37. Left and right eyepieces, 46 and 47, are provided in the stereo vision display 45 so that the user may view left and right two-dimensional ("2D") display screens inside the display 45 respectively with the user's left and right eyes.

The processor 43 performs various functions in the medical robotic system. One important function that it performs is to translate and transfer the mechanical motion of input devices 41, 42 to command actuators in their associated device manipulators to actuate their respective joints so that the Surgeon can effectively manipulate devices, such as the tool instruments 31, 33, 35 and endoscope 37, which are associated with the input devices 41, 42 at the time. Another function of the processor 43 is to implement the methods, cross-coupling control logic, and controllers described herein.

Although described as a processor, it is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the Console, the processor 43 may also be distributed as subunits throughout the system 3000.

U.S. Pat. No. 6,659,939 B2 entitled "Cooperative Minimally Invasive Telesurgical System," which is incorporated herein by reference, provides additional details on a multiple aperture medical robotic system such as described herein.

FIG. 12 illustrates, as an example, the Image Capturing System 3020 which has a robot or movable arm 1101 which is mounted to a base 1106. The robot arm 1101 comprises a carousel 1107, first link 1102, second link 1103, wrist 1104, and C-arm 1105. The carousel 1107 is rotatable (as indicted by arrow "a") relative to the base 1106 using a carousel joint 1108. The first link 1102 is rotatable (as indicated by arrow "b") relative to the carousel 1107 using a shoulder joint 1109. The second link 1103 is rotatable (as indicated by arrow "c") relative to the first link 1102 using an elbow joint 1110. The wrist 1104 is rotatable (as indicated by arrow "d") relative to the second link 1103 using a roll joint 1111. The C-arm 1105 is rotatable (as indicated by arrow "e") relative to the wrist 1104 using a pitch joint 1112 and rotatable (as indicated by arrow "j") relative to the wrist 1104 using a yaw joint 1121.

The C-arm 1105 comprises a first limb 1113, second limb 1114, and a central portion 1115. The first and second limbs 1113, 1114 are extendable away from and towards (as indicated by arrow "f") the central element 1115 using an extender joint 1120. The first limb 1113 has an X-ray detector 1116 disposed at its distal end and the second limb 1114 has an X-ray source 1117 disposed at its distal end. The X-ray detector 1116 is rotatable (as indicated by arrow "g") relative to the distal end of the first limb 1113. The X-ray source 1117 is rotatable (as indicated by arrow "h") relative to the distal end of the second limb 1114. In this arrangement, the X-ray source and X-ray detector are disposed on opposing ends of the C-arm 1105 so as to form an image capturing device. By actuating the carousel joint 1108, shoulder joint 1109, elbow joint 1110, roll joint 1111, pitch joint 1112, yaw joint 1121, and extender joint 1120, the C-arm 1105 may be positioned relative to the Patient so that the C-arm 1105 may be moved so that the image capturing device (comprising X-ray source 1117 and X-ray detector 1116) may capture a series of two-dimensional projections of one or more objects within a specified region of interest at a work site in the Patient. The series of two-dimensional projections may then be used to generate a three-dimensional computer model of the one or more objects in a conventional manner for cone beam computed tomography.

Previously incorporated by reference U.S. Published Application 2009/0234444 A1 provides additional details on such an Image Capturing System and its use during the performance of a medical procedure on a patient.

FIG. 13 illustrates, as an example, an alternative Patient-Side Cart 4010 which is usable in the robotic system 3000 to introduce a plurality of articulated instruments to a work site through a single entry aperture in the Patient by an entry guide 200. The aperture may be a minimally invasive incision or a natural body orifice. The entry guide 200 is a cylindrical structure which is held and manipulated by a robot arm 4011, which is mounted on base 4015 and includes a setup arm 4012 and an entry guide manipulator 4013. The setup arm 4012 comprises a plurality of links and joints which are used to position the entry guide 200 at the aperture. As indicated in the figure, the setup arm 4012 includes a prismatic joint for adjusting the height of the setup arm 4012 (as indicated by arrow "A") and a plurality of rotary joints for adjusting the horizontal position of the setup arm 4012 (as indicated by arrows "B" and "C"). The entry guide manipulator 4013 is used to robotically pivot the entry guide 200 (and the articulated instruments disposed within it at the time) in yaw, pitch and roll angular rotations about the pivot point as indicated by arrows D, E and F, respectively. Articulated instrument manipulators (not shown) reside in housing 4014.

As shown in FIG. 14, the entry guide 200 has articulated instruments such as articulated surgical instruments 231, 241 and an articulated stereo camera instrument 211 (or other image capturing device instrument) extending out of its distal end. The camera instrument 211 has a pair of stereo image capturing elements 311, 312 and a fiber optic cable 313 (coupled at its proximal end to a light source) housed in its tip. The surgical instruments 231, 241 have working ends 331, 341. Although only two instruments 231, 241 are shown, the entry guide 200 may guide additional instruments as required for performing a medical procedure at a work site in the Patient. For example, as shown in a cross-sectional view of the entry guide 200 in FIG. 15, a passage 351 is available for extending another articulated surgical tool through the entry guide 200 and out through its distal end. Passages 431, 441, are respectively used by the articulated surgical tool instruments 231, 241, and passage 321 is used for the articulated camera instrument 211.

When the Patient-Side Cart 4010 is used in the robotic system 3000, the stereo vision display 45 of the Console 3030 displays stereo images derived from the stereo images captured by the articulated camera instrument 211. Also, the processor 43 of the Console 3030 translates and transfers the mechanical motion of the input devices 41, 42 to actuate joints of devices, such as the entry guide 200, articulated surgical instruments 231, 241, and articulated camera instrument 211, which are associated at the time with the input devices 41, 42.

Each of the articulated instruments comprises a plurality of actuatable joints and a plurality of links coupled to the joints. As an example, as shown in FIG. 14, the second articulated instrument 241 comprises first, second, and third links 322, 324, 326, first and second joints 323, 325, and a wrist assembly 327. The first joint 323 couples the first and second links 322, 324 and the second joint 325 couples the second and third links 324, 326 so that the second link 324 may pivot about the first joint 323 in pitch and yaw while the first and third links 322, 326 remain parallel to each other. The first articulated instrument 231 and the camera articulated instrument 211, may be similarly constructed and operated.

U.S. Pat. No. 7,725,214 entitled "Minimally Invasive Surgical System," which is incorporated herein by reference, provides additional details on a single aperture medical robotic system such as described herein.

Now referring back to FIG. 1, a block diagram of components of the robotic system 1000 is illustrated to describe various aspects of the present invention. In this example, the robotic system 1000 has a first manipulatable device 1001, a first image capturing device 1002, and a camera 1003. The first manipulatable device 1001 may be an instrument such as the one of the instruments 33, 35 held and manipulated by robot arms of the Patient-Side Cart 3010. Alternatively, the first manipulatable device 1001 may be an entry guide through which articulated instruments extend such as the entry guide 200 held and manipulated by the robot arm of the Patient-Side Cart 4010. A second manipulatable device 1004 is also shown which may be another device such as the first manipulatable device 1001. A second image capturing device 1005 is also shown which may provide a different imaging modality than that of the first image capturing device 1002. Although two manipulatable devices and two image capturing devices are shown for illustrative purposes, it is to be appreciated that in practice, more or less of each of such devices may be included in the robotic system 1000 to perform a task or procedure on an object at a work site. Additional cameras may also be included.

A device controller 1021 controls movement of the robot arm 1011 to position and orient a working end of the first manipulatable device 1001 in response to commands from an input unit 1031. The input unit 1031 may be a user operated input device, such as one of the input devices 41, 42 or the foot pedal 44 of the console 3030. Alternatively, the input unit 1031 may be a processor, such as the processor 43 of the console 3030, executing stored program instructions. Alternatively, the input unit 1031 may be coupled control logic which communicates through bus 1040 with one or more of the controllers 1022, 1023, 1024, 1025 and/or input units 1032, 1033, 1034, 1035 associated with the first image capturing device 1002, the camera 1003, the second manipulatable device 1004, and the second image capturing device 1005.

Likewise, a device controller 1024 controls movement of the robot arm 1014 to position and orient a working end of the second manipulatable device 1004 in response to commands from an input unit 1034. The input unit 1034 may be a user operated input device, such as one of the input devices 41, 42 or the foot pedal 44 of the console 3030. Alternatively, the input unit 1034 may be a processor, such as the processor 43 of the console 3030, executing stored program instructions. Alternatively, the input unit 1034 may be coupled control logic which communicates through bus 1040 with one or more of the controllers 1021, 1022, 1023, 1025 and/or input units 1031, 1032, 1033, 1035 associated with the first manipulatable device 1001, the first image capturing device 1002, the camera 1003, and the second image capturing device 1005.

The first image capturing device 1002 is manipulatable by its robot arm 1012 (or other motorized mechanism) to capture a plurality of two-dimensional image slices or projections of an object at the work site from which a three-dimensional model of the object may be computer generated without prior knowledge of the shape of the object using an imaging modality such as ultrasound, X-ray fluoroscopy, Computed Tomography (CT), and Magnetic Resonance Imaging (MRI). A controller 1022 controls movement of the robot arm 1012 to position and orient the first image capturing device 1002 in response to commands from an input unit 1032. The input unit 1032 may be a user operated input device, such as one of the input devices 41, 42 of the console 3030. Alternatively, the input unit 1032 may be a processor, such as the processor 43 of the console 3030, executing stored program instructions. Alternatively, the input unit 1032 may be coupled control logic which communicates through bus 1040 with one or more of the controllers 1021, 1023, 1024, 1025 and/or input units 1031, 1033, 1034, 1035 associated with the first manipulatable device 1001, the camera 1003, the second manipulatable device 1004, and the second image capturing device 1005. The first image capturing device 1002 and its robot arm 1012 may be combined to form an image capturing system such as the Image Capturing System 3020.

The second image capturing device 1005 may be similarly constructed and operated as the first image capturing device 1002 to capture a plurality of two-dimensional image projections of an object at the work site from which a three-dimensional model of the object may be computer generated without prior knowledge of the shape of the object using an imaging modality such as ultrasound, X-ray fluoroscopy, Computed Tomography (CT), and Magnetic Resonance Imaging (MRI). Typically, different imaging modalities are provided by the first and second image capturing devices 1002, 1005. When similarly constructed as the first image capturing device 1002, a controller 1025 controls movement of the robot arm 1015 to position and orient the second image capturing device 1005 in response to commands from an input unit 1035. The input unit 1035 may be a user operated input device, such as one of the input devices 41, 42 of the console 3030. Alternatively, the input unit 1035 may be a processor, such as the processor 43 of the console 3030, executing stored program instructions. Alternatively, the input unit 1035 may be coupled control logic which communicates through bus 1040 with one or more of the controllers 1021, 1022, 1023, 1024, and/or input units 1031, 1032, 1033, 1034, associated with the first manipulatable device 1001, the first image capturing device 1002, the camera 1003, and the second manipulatable device 1004. The second image capturing device 1005 and its robot arm 1015 may be combined to form an image capturing system such as the Image Capturing System 3020.

Alternatively, the second image capturing device 1005 may be constructed differently than that of the first image capturing device 1002. For example, the second image capturing device 1005 may be held, positioned, and oriented by one of the first and second manipulatable devices 1001, 1004 rather than having its own robot arm, controller, and input unit. Examples of such a second image capturing device include a drop-in ultrasound probe or an optical coherent tomography probe. For details of such an ultrasound probe, see, e.g., U.S. 2007/0021738 A1 entitled "Laparoscopic Ultrasound Robotic Surgical System," which is incorporated herein by reference.

The camera 1003 may be held and manipulated by a robot arm 1013 to capture stereoscopic images of work site, such as the endoscope 37 of FIG. 9. As an alternative example, the camera 1003 may be the articulated camera instrument 211 of FIG. 14. A controller 1023 controls movement of the robot arm 1013 (or joints of the articulated camera instrument 211) to position and orient an image capturing element of the camera 1003 in response to commands from an input unit 1033. The input unit 1033 may be a user operated input device, such as one of the input devices 41, 42 of the console 3030. Alternatively, the input unit 1033 may be a processor, such as the processor 43 of the console 3030, executing stored program instructions. Alternatively, the input unit 1033 may be coupled control logic which communicates through bus 1040 with one or more of the controllers 1021, 1022, 1024, 1025 and/or input units 1031, 1032, 1034, 1035 associated with the first manipulatable device 1001, the image capturing device 1002, the second manipulatable device 1004, and the second image capturing device 1005.

Alternatively, the camera 1003 may be held, positioned, and oriented by one of the first and second manipulatable devices 1001, 1004 rather than having its own robot arm, controller, and input unit. For example, the camera may be a tethered camera which is orientable by a manipulatable device pulling on the tether(s). In this case, the camera would not have its own robot arm, controller, and input unit. An example of such a tethered camera is described in U.S. Patent Application Publication No. 2012/02900134, entitled "Estimation of a Position and Orientation of a Frame Used in Controlling Movement of a Tool," which is incorporated herein by reference.

Each of the robot arms 1011, 1012, 1013, 1014, 1015 includes a plurality of links and a plurality of actuatable joints whose positions and/or velocities are sensed by a plurality of joint sensors. Information from the plurality of joint sensors of each robot arm 1011, 1012, 1013, 1014, 1015 is provided to its respective controller 1021, 1022, 1023, 1024, 1025 for control purposes and may be provided to one or more of the other controllers over bus 1040 for collision avoidance purposes, since this joint information indicates configuration information for the robot arms 1011, 1012, 1013, 1014, 1015.

Each of the control units 1021-1025 may include at least one processing unit and memory. In some examples, the processing unit may control operation and/or execution of hardware and/or software in the respective control unit 1021-1025. Each of the processing units may include one or more central processing units (CPUs), multi-core processors, microprocessors, microcontrollers, digital signal processors, field programmable gate arrays (FPGAs), custom processors/application specific integrated circuits (ASICs), and/or the like. The memory may be used to store one or more software and/or firmware applications as well as various data structures to be used by the respective control unit 1021-1025. The memory may also include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

The robotic system 1000 also includes a stereo viewer or display 1051 for displaying stereo images which have been generated by an image processor 1050 from images captured by the stereo camera 1003 and/or three-dimensional computer models of one or more objects which have been generated by the image processor 1050 from the plurality of two-dimensional image slices of the one or more objects captured by the first image capturing device 1002 and/or second image capturing device 1005. Before displaying images derived from both the camera 1003 and one or both of the first and second image capturing devices 1002, 1005 concurrently on the display 1051, the image processor 1050 registers the images so that the three-dimensional computer models of the one or more objects are properly superimposed on and positioned relative to images of the one or more objects in the stereo images derived from images captured by the stereo camera 1003.

FIGS. 3, 4 respectively illustrate, as examples, flow diagrams of methods 2000, 2500 which may be implemented in the robotic system 1000 for avoiding a collision between independently operated image capturing device and manipulatable device robot arms. Although shown for explanatory purposes as two different methods, it is to be appreciated that the methods 2000, 2500 are essentially the same method taken from different perspectives. In particular, the method 2000 is from the perspective of an image capturing device reference frame and may be performed by an image capturing device controller and the method 2500 is from the perspective of a manipulatable device reference frame and may be performed by a manipulatable device controller.

Although only one manipulatable device is mentioned in describing the methods herein, it is to be appreciated that when the working end of more than one device is viewable within the field of view of the image capturing device, each of those devices are to be processed as the described manipulatable device according to the methods so that collisions may be avoided between their robot arms and the robot arm of the image capturing device. For example, when the robotic system 1000 is the medical robotic system 3000 of FIG. 8 and it includes the Patient-Side Cart 3010 of FIG. 9, the relevant blocks of both methods 2000, 2500 are performed for each of the manipulatable devices 31, 33, 35, 37 that is viewable in images captured by the image capturing device 3020. On the other hand, when the robotic system 1000 is the medical robotic system 3000 of FIG. 8 and it includes the Patient-Side Cart 4010 of FIG. 13, the relevant blocks of both methods 2000, 2500 are performed for the entry guide manipulator 4013, but the working ends of articulated instruments extending out of the entry guide 200 are treated as the working end of the entry guide 200.

To avoid confusion and unintended consequences, only one of the methods 2000, 2500 is performed to avoid collisions between robot arms. Also, only one of the device controllers preferably performs the collision avoidance method. The controller taking such action may be pre-established, user selected, or selected by certain criteria.

As an example of user specification, when the robotic system 1000 is the medical robotic system 3000 of FIG. 8 and it includes the Patient-Side Cart 3010 of FIG. 9, the Surgeon may interact with a menu being displayed on the stereo viewer 45 to select either the control unit 3021 to perform the method 2000 or the processor 43 to perform the method 2500. As previously explained, the control unit 3021 controls movement of the robot arm 1101 which holds and manipulates the image capturing device 1116, 1117 of the Image Capturing System 3020. The processor 43, on the other hand, implements a controller which controls movement of the robot arm 34 that holds and manipulates the instrument 33, which may be the manipulatable device for the purpose of this example.

When the robotic system 1000 is the medical robotic system 3000 of FIG. 8 and it includes the Patient-Side Cart 4010 of FIG. 13, then the manipulatable device referred to in methods 2000, 2500 is the entry guide 200 rather than one of the articulated instruments 211, 231, 241. In this case, it is the entry guide manipulator 4013 that is at risk of colliding with or being struck by the robot arm 1101 of the Image Capturing System 3020. The articulated instruments 211, 231, 241 do not have significant portions of any robot arms extending outside the Patient's body. They merely have manipulators whose movements are generally confined to be within a housing area 4014 of the entry guide manipulator 4013 as shown in FIG. 13. It is notable that collision avoidance between the robot arm 1101 of the Image Capturing System 3020 and the entry guide manipulator 4013 may be simpler than collision avoidance between the robot arm 1101 of the Image Capturing System 3020 and the robot arms 32, 34, 36, 38 of the Patient-Side Cart 3010. This is because not only are there more robot arms 32, 34, 36, 38 of the Patient-Side Cart 3010 for the robot arm 1101 of the Image Capturing System 3020 to collide with, but also because the robot arms 32, 34, 36, 38 of the Patient-Side Cart 3010 may move more often than the entry guide robot manipulator 4013 of the Patient-Side Cart 4010.

FIG. 2 illustrates, as an example, a flow diagram of a method 9000, which is implemented in the robotic system 1000, for registering an image capturing device robot arm and a manipulatable device robot arm. Using the method, higher accuracy registrations are performed as the image capturing device robot arm moves closer to the manipulatable device robot arm. This multi-step approach provides high accuracy registration in a safe manner.

In block 9001, the method performs a low accuracy registration (e.g., within an accuracy range of tens of centimeters) of the image capturing device robot arm and the manipulatable device robot arm relative to a common reference frame at their initial positions using an external tracker system and kinematic data for the robot arms. As an example, the external tracker system may be of the transmitter/receiver type which conventionally employs transmitters, which are strategically disposed on known locations of the robot arms of the image capturing device and the manipulatable device, and one or multiple receivers, which are disposed within transmission distance of the transmitters. As another example, the external tracker system may be of the optical type which conventionally employs optically discernible targets, which are strategically disposed on known locations of the robot arms of the image capturing device and the manipulatable device, and one or multiple optical detectors, which are disposed so as to have an unobstructed view of the targets. The kinematic data may be provided, for example, by encoders disposed to sense joint positions of the image capturing device robot arm and the manipulatable device robot arm. The joint positions may then be combined in a conventional manner using knowledge of the construction, shapes, and sizes of the robot arms to estimate the configurations of the robot arms.

In block 9002, the image capturing device is moved towards the manipulatable device robot arm to assume a low-risk setup position that is close enough to allow the image capturing device being held by the image capturing device robot arm to capture images of at least a portion of the manipulatable device robot arm while being sufficiently far enough away from the manipulatable device robot arm to ensure that the image capturing device robot arm does not collide with the manipulatable device robot arm. In determining the low-risk setup position, the method also takes into account the current low accuracy level of the registration through a first safety margin that ensures no collision will occur between the image capturing device robot arm and the manipulatable device robot arm. For example, the first safety margin may maintain a distance of at least ten centimeters between the image capturing device robot arm and the manipulatable device robot arm to account for the current low accuracy in determining the relative positions of those two robot arms. The movement of the image capturing device robot arm may be performed, for example, by an operator commanding such movement through a robot arm controller with assistance from the robot arm controller to inhibit unsafe movement. For example, the robot arm controller may provide force feedback to the operator through a haptic device, such as a joystick, to provide resistance against the unsafe movement. Alternatively, it may be performed automatically by the robot arm controller in either a direct mode or cross-coupled mode.

In block 9003, the method performs a mid accuracy registration (e.g., within an accuracy range of centimeters) of the image capturing device robot arm and the manipulatable device robot arm relative to the common reference frame at their current positions using one or more captured images of at least a part of the manipulatable device robot arm and kinematics data for the robot arms.

In block 9004, the method then waits for an operator's command to initiate movement of the image capturing device robot arm to capture images of a user specified region of interest.

In block 9005, the image capturing device is moved towards the manipulatable device robot arm to assume an image capturing setup position that is close enough to allow the image capturing device being held by the image capturing device robot arm to capture images of a user specified region of interest while being sufficiently far enough away from the manipulatable device robot arm to ensure that the image capturing device robot arm does not collide with the manipulatable device robot arm. In determining the image capturing setup position, the method takes into account the current mid accuracy level of the registration through a second safety margin that ensures no collision will occur between the image capturing device robot arm and the manipulatable device robot arm. For example, the second safety margin may maintain a distance of at least one centimeter between the image capturing device robot arm and the manipulatable device robot arm to account for the current mid accuracy in determining the relative positions of those two robot arms. The movement of the image capturing device robot arm may be performed, for example, by an operator commanding such movement through a robot arm controller with assistance from the robot arm controller to inhibit unsafe movement. For example, the robot arm controller may provide force feedback to the operator through a haptic device, such as a joystick, to provide resistance against the unsafe movement. Alternatively, the movement may be performed automatically by the image capturing device controller directly or through a coupled control mode with the manipulatable device controller.

In block 9006, the method commands the image capturing device robot arm to move relative to the region of interest and commands the image capturing device being held by the image capturing device robot arm to capture images of the region of interest during such movement while avoiding a collision of the image capturing device robot arm and the manipulatable device robot arm. In addition to capturing images of the region of interest, the image capturing device captures images of at least a working end of a manipulatable device being held by the manipulatable device robot arm. In this case, the working end of the manipulatable device is proximate to the region of interest so as to be within the field of view of the image capturing device. During the image capturing process, the method performs at least one high accuracy registration (e.g., within an accuracy range of millimeters) of the image capturing device robot arm and the manipulatable device robot arm relative to the common reference frame at their current positions using one or more of the captured images of the working end of the manipulatable device and kinematics data for the robot arms.

Additional details describing aspects of block 9006 are described below in reference to FIGS. 3, 4 and additional details describing aspects of blocks 9005, 9006 are described below in reference to FIG. 5.

Referring now to the method 2000 of FIG. 3, in block 2001, the method, which is preferably performed by the image capturing device controller 1022, receives information of the configuration of the robot arm that holds and manipulates the image capturing device. When the robot arm comprises a plurality of links coupled together by a plurality of joints, the robot arm configuration is determinable from sensed positions of the joints and known geometries of the links and other structure making up the robot arm. As previously described in reference to FIG. 1, such robot arm configuration information may be provided from a plurality of sensors in the image capturing device robot arm, such as encoders which are coupled to actuators of the joints. Alternatively, it may be joint positions being commanded by the image capturing device controller 1022 in response to commands from the input device 1032.

In block 2002, the method determines whether or not it is time to perform a registration of the image capturing device to the manipulatable device. Such registration may be performed once at the start of the method or it may be performed periodically to correct any registration errors that may accrue over time. If the determination in block 2002 is YES, then the method performs the registration by performing blocks 2003, 2004. On the other hand, if the determination in block 2002 is NO, then registration is skipped by the method jumping to block 2005.

In block 2003, the method receives an image, which has been captured by the image capturing device, of the working end of the manipulatable device. Generally, the received image will be a two-dimensional slice or projection of the working end of the manipulatable device and any other objects within an image capturing cone of the image capturing device.

In block 2004, the method determines the position and orientation (i.e., pose) of the working end of the manipulatable device relative to a reference frame of the image capturing device, which corresponds to a position and orientation of the image capturing cone or field of view of the image capturing device. To do this, the method conventionally uses artificial and/or natural features of the working end that are discernible in the received image. In this case, artificial features include such things as markings or structure specifically placed on the working end to aid in determining their pose (i.e., position and orientation). Natural features include such things as the shape and known geometries of structure of the working end of the manipulatable device. The pose of the working end may be determinable even though the working end may be partially occluded. For example, the working end may be occluded by portions of a patient's anatomy, other portions of the manipulatable device, portions of the image capturing device, other medical instruments, and/or the like. The patient's anatomy may include soft tissue, bone, teeth, and/or the like. To aid in the determination, the sequence of images captured by the image capturing device and received as the method loops through blocks 2001-2009 may be used to refine the determination of the pose. Also, conventional tool tracking techniques may be used that aid in and serve to further refine the determination of the pose of the working end of the manipulatable device. For additional details on such pose determining techniques and artifacts, see U.S. Pat. No. 8,108,072 entitled "Methods and systems for robotic instrument tool tracking with adaptive fusion of kinematics information and image information," which is incorporated herein by reference, and U.S. Publication No. 2010/0168763 A1 entitled "Configuration marker design and detection for instrument tracking," which is incorporated herein by reference.

In block 2005, the method receives information of the configuration of the robot arm that holds and manipulates the manipulatable device. Where the robot arm comprises a plurality of links coupled together by a plurality of joints, the robot arm configuration is determinable from sensed positions of the joints and known geometries of the links and other structure making up the robot arm. As previously described in reference to FIG. 1, such robot arm configuration information may be provided from a plurality of sensors of the manipulatable device robot arm, such as encoders which are coupled to actuators of the joints. Alternatively, it may be joint positions being commanded by the manipulatable device controller 1021 in response to commands from the input device 1031. Alternatively, it may be some joint positions being provided by tracking the working end of instruments in endoscopic images which may provide better accuracy compared to encoder measurements.

If the manipulatable device robot arm is a redundant degree-of-freedom (DOF) arm, then the information of the configuration of the robot arm preferably includes either the sensed joint positions or commanded joint positions of the manipulatable device robot arm. If, on the other hand, there is only one robot arm configuration that may correspond to the pose of the working end of its held manipulatable device, then the robot arm configuration may theoretically be determined from the determined pose of the working end of the manipulatable device, the known construction and geometries (e.g., size and shape) of the manipulatable device and its robot arm, and the position of the base of the manipulatable device robot arm. In this case, it may not be necessary to receive information of the sensed or commanded joint positions in block 2005, only the base position of the manipulatable device robot arm is necessary. When the manipulatable device robot arm is mounted to a base that doesn't move, then the base position is fixed and only needs to be determined once and stored in a memory. When the manipulatable device robot arm is mounted to a movable base, then the base position may be determined, for example, by external sensors such as pressure sensors strategically disposed on the floor. As another example, the base position may be determined by a transmitter/receiver system in which one or more transmitters are disposed on the base with one or more receivers disposed at fixed locations. As another example, the base position (as well as the robot arm configuration) may be determined by an optical tracking system or by any other well known position sensing means.

In block 2006, the method determines the configuration and position of the manipulatable device robot arm in the image capturing device frame of reference. Since the pose of the working end of the manipulatable device relative to the image capturing device reference frame has already been determined in block 2004, the determination of the configuration and position of its robot arm in the image capturing device frame of reference is determined in this case by using the known construction and geometries of the manipulatable device and its robot arm along with the information of the manipulatable device robot arm configuration received in block 2005.

In block 2007, the method determines the configuration and position of the image capturing device robot arm in the image capturing device reference frame. Since the image capturing device reference frame is defined by the pose of the distal end of the image capturing device robot arm, it is a simple matter to determine the configuration and position of the image capturing device robot arm in the image capturing device reference frame using the known construction and geometries of the image capturing device and its robot arm along with the information of the image capturing device robot arm configuration received in block 2001.

In block 2008, the method determines whether an imminent collision is threatened between the image capturing device robot arm and the manipulatable device robot arm. Preferably, the determination is made by using the information received or determined in blocks 2001-2007 for the current process cycle and previous process cycles. By using time series information, not only can the trajectories of the two arms be predicted, but the rates at which they are moving may be estimated. With this information, a collision prediction may be made. When the predicted collision is within a specified time period, then the collision is considered to be imminent, requiring immediate action. The collision prediction may use a minimum distance between the image capturing device robot arm and the manipulatable device robot arm. In determining the minimum, the method preferably approximates links of the robot arms with geometric shapes that are dimensionally slightly larger than the actual links for safety purposes. Since the geometric shapes of the image capturing device robot arm and the geometric shapes of the manipulating device robot arm occupy known positions and orientations relative to each other at this point, it is a straightforward calculation to determine a minimum distance between the geometric shapes representing the image capturing device robot arm and the geometric shapes representing the manipulating device robot arm.

One or ordinary skill would also understand that the determination of block 2008 may be used to detect additional undesirable relationships between the manipulating device robot arm and the image capturing device robot arm other than an imminent collision. In some embodiments, block 2008 may be used to detect when the manipulating device robot arm and the image capturing device robot arm are in too close a proximity to each other, even though a collision is not imminent. In some embodiments, block 2008 may be used to detect that the manipulating device robot arm is obstructing a region of interest for which the image capturing device is to capture images thereof.

If the determination block 2008 is NO, then the method jumps back to block 2001 to perform blocks 2001-2008 for a next process cycle. On the other hand, if the determination is YES, then in block 2009, the method commands the image capturing device robot arm to take an action to avoid a collision with the robot arm of the manipulatable device. The commanded action may be to temporarily halt movement of the image capturing device robot arm until the manipulatable device robot arm has moved to a collision safe position. Alternatively, rather than halting all movement of the image capturing device robot arm, the speed of its movement may be adjusted instead to avoid collision with the manipulatable device robot arm. Alternatively, if the image capturing device robot arm is a redundant DOF arm, then an alternative arm configuration may be commanded to avoid collision with the manipulatable device robot arm. Alternatively, the movement of the image capturing device robot arm may be halted and the collision avoidance task may be passed over to the manipulatable device controller to perform the method 2500 of FIG. 4.

After performing block 2009, the method then loops back to block 2001 to process information for a next process cycle.

Referring now to the method 2500 of FIG. 4, in block 2501, the method, which is preferably performed by the manipulatable device controller 1021, receives information of the configuration of the robot arm that holds and manipulates the manipulatable device. Where the robot arm comprises a plurality of links coupled together by a plurality of joints, the robot arm configuration is determinable from sensed positions of the joints and known geometries of the links and other structure making up the robot arm. As previously described in reference to FIG. 1, such robot arm configuration information may be provided from a plurality of sensors in the image capturing device robot arm, such as encoders which are coupled to actuators of the joints. Alternatively, it may be joint positions being commanded by the manipulatable device controller 1021 in response to commands from the input device 1031. Alternatively, it may be some joint positions being provided by tracking the working end of instruments in endoscopic images which may provide better accuracy compared to encoder measurements.

In block 2502, the method determines whether or not it is time to perform a registration of the image capturing device to the manipulatable device. Such registration may be performed once at the start of the method or it may be performed periodically to correct any registration errors that may accrue over time. If the determination in block 2502 is YES, then the method performs the registration by performing blocks 2503, 2504. On the other hand, if the determination in block 2502 is NO, then registration is skipped by the method jumping to block 2505.

In block 2503, the method receives an image, which has been captured by the image capturing device, of the working end of the manipulatable device. Generally, the received image will be a two-dimensional slice or projection of the working end of the manipulatable device and any other objects within an image capturing cone or field of view of the image capturing device. As an example, the image may be received by the manipulatable device controller 1021 over a bus 1040 (or cable 3050 of FIG. 8) from the first image capturing device 1002 or a processor in an image capturing system that includes the first image capturing device 1002.

In block 2504, the method determines the position and orientation (i.e., pose) of the working end of the manipulatable device relative to a reference frame of the image capturing device in the same manner as described in reference to block 2004 of FIG. 3.

In block 2505, the method receives information of the configuration of the robot arm that holds and manipulates the image capturing device. Where the robot arm comprises a plurality of links coupled together by a plurality of joints, the robot arm configuration is determinable from sensed positions of the joints and known geometries of the links and other structure making up the robot arm. As previously described in reference to FIG. 1, such robot arm configuration information may be provided from a plurality of sensors of the manipulatable device robot arm, such as encoders which are coupled to actuators of the joints. Alternatively, it may be joint positions being commanded by the image capturing device controller 1022 in response to commands from the input device 1032.

In block 2506, the method determines the configuration and position of the manipulatable device robot arm in the manipulatable device reference frame. Since the manipulatable device reference frame is defined by the pose of the distal end of the manipulatable device robot arm, it is a simple matter to determine the configuration and position of the manipulatable device robot arm in the manipulatable device reference frame using the information received in block 2501 and the known construction and geometries of the manipulatable device and its robot arm.

In block 2507, the method determines the configuration and position of the image capturing device robot arm in the manipulatable device frame of reference. One way to do this is to first determine the configuration and position of the image capturing device robot arm in the image capturing device reference frame, such as determined in block 2007 of FIG. 3, then use the following transformation equation to translate points of the image capturing device robot arm from the image capturing device reference frame to manipulatable device reference frame:

$$^{M}P = {^{M}_{I}T}\, {^{I}P} \qquad (1)$$

where $^MP$ is a point in the manipulatable device reference frame "M", $^M_IT$ is the image capturing device reference frame "I" to manipulatable device reference frame "M" transform, and $^IP$ is a point in the image capturing device reference frame "I".

The method may determine the transform $^M_IT$ by comparing points of the working end of the manipulatable device in the image reference frame, using information of its pose determined in block 2504, with corresponding points of the working end of the manipulatable device in the manipulatable device reference frame, using information of its pose determined from the information of the manipulatable device robot arm configuration which was received in block 2501 and prior known information of the size, shape, and construction of the manipulatable device. For additional details on such reference frame transformations, see previously incorporated by reference U.S. Patent Application Publication No. 2012/02900134, entitled "Estimation of a Position and Orientation of a Frame Used in Controlling Movement of a Tool."

In block 2508, the method determines whether an imminent collision is threatened between the image capturing device robot arm and the manipulatable device robot arm in a similar manner as described in reference to block 2008 of FIG. 3. One of ordinary skill would also understand that similar to the determination of block 2008, block 2508 may also be used to detect additional undesirable relationships between the manipulating device robot arm and the image capturing device robot arm other than an imminent collision.

If the determination block 2508 is NO, then the method jumps back to block 2501 to perform blocks 2501-2509 for a next process cycle. On the other hand, if the determination is YES, then in block 2509, the method may command either the manipulatable device robot arm or the image capturing device robot arm, through the image capturing device controller 1022, to take a collision avoidance action. The entity performing the collision avoidance action and the particular collision avoidance action taken may take different forms depending upon system factors. One factor is the nature of the tasks being performed at the time by the image capturing device and the manipulatable device. Another factor is the type or structure of the robot arms or their corresponding velocity and acceleration at the moment when an imminent collision is detected.

As an example of the nature of the tasks being performed at the time by the image capturing device and the manipulatable device, if the robotic system 1000 is the medical robotic system 3000 and the manipulatable device is one of the instruments 33, 35 which is being used at the time to perform a delicate surgery on a Patient, then it is desirable not to disturb the robot arm holding the instrument. Therefore, in this case it may be preferable to take action by modifying the trajectory of the image capturing device robot arm 1101 to avoid a collision. To avoid such collision, movement of the image capturing device robot arm 1101 may be temporarily halted until the manipulatable device robot arm has moved to a collision safe position. Alternatively, rather than halting all movement of the image capturing device robot arm 1101, the speed and/or direction of its movement may be adjusted instead to avoid collision with the manipulatable device robot arm.

As an example of the type or structure of the robot arms, if either or both of the image capturing device and manipulatable device robot arms has redundant degrees-of-freedom (DOF), then one of the robot arms with such redundant DOF may be configured in an alternative configuration without affecting the pose of its held device. In particular, if the manipulatable device robot arm has redundant DOF, then it would not be necessary to modify the trajectory of the image capturing device since the manipulatable device robot arm may be configured instead to an alternative configuration without significantly impacting the manipulation of its held manipulatable device. When both the image capturing device and manipulatable device robot arms have redundant DOF, then one of the first and second robot arms is selected for using an alternative configuration to avoid the imminent collision by processing differences between current configurations of the first and second robot arms and their respective pluralities of possible configurations to minimize a cost function. Alternatively, the selection may be made by processing required joint movements of the first and second robotic systems to move from their current configurations to others of their respective pluralities of possible configurations to minimize a cost function.

Any of several possible cost functions may be minimized by the selection of an alternative configuration. One possible cost function may be based on an inverse square of the minimum distance between the first and second robot arms. A second possible cost function may be based on a weighted average of an inverse square of distances between links of the first and second robot arm, with each link being associated with a passive or active degree of freedom. A third possible cost function may be based on the second cost function, but may account for only distances which are below a threshold, such as a threshold within an order of magnitude of a desired safety margin. A fourth possible cost function may be based on a modified version of the second cost function where the distances are measured between virtual objects or buffer regions surrounding the links of the first and second robot arms. A fifth possible cost function may include the buffer regions of the fourth cost function and the distance threshold of the third cost function. A sixth possible cost function may be based on a constrained manipulability index for the first and second robot arms with the manipulability index estimating an ability of the first or second robot arm to move in arbitrary directions around the alternative configuration. A seventh possible cost function may be based on virtual potential fields applied to the links and/or joints of the first and second robot arms. As an example, each link and/or joint of the first and second robot arms may have a virtual electric charge assigned to it and the induced virtual repelling force may be integrated between the first and second robot arms to determine the seventh cost function.

After performing block 2509, the method then loops back to block 2501 to process information for a next process cycle.

During or after the performance of methods 2000, 2500, an update or recalibration of initial registration transforms for work site objects may be performed. For example, if the robotic system 1000 is the medical robotic system 3000, then it is common practice to register each of the work site objects to a world reference frame. In this case, the work site objects include the instruments 31, 33, 35, the endoscope 37, the image capturing device 1116, 1117 of the Image Capturing System 3020, and the Patient's anatomy. During the performance of a procedure, however, registration errors may accumulate or otherwise occur in some manner. Thus, it may be beneficial to update their initial registration transforms with respect to the fixed reference frame using images of the working ends of the instruments 31, 33, 35 and the endoscope 37, which have been captured by the Image Capturing System 3020.

In the methods 2000, 2500 of FIGS. 2, 3, the image capturing device and the manipulatable device are independently operated typically by different people. For example, when the robotic system 1000 is the medical robotic system 3000, an Assistant standing next to the Operating Table 3040 may operate the control unit 3021 to control movement of the Image Capturing System 3020 and the Surgeon may operate the input devices 41, 42 of the Console 3030 to control movement of the manipulatable devices 33, 35. However, it may be desirable at times for the Surgeon to also control movement of the Image Capturing System 3020 during the performance of a medical procedure. For example, when endoscopic images of an exterior view of an anatomical structure are being displayed on the stereo viewer 45 of the Console 3030, the Surgeon may want to supplement those images with three-dimensional X-ray images of an interior view of the anatomical structure. However, since the Surgeon is occupied with the performance of the medical procedure, a method for automatically controlling the Image Capturing System 3020 to provide the Surgeon's desired view of a region of interest is useful.

FIG. 5 illustrates, as an example, a method 4000 implemented in the robotic system 1000 for automatically controlling movement of the image capturing device so as to capture images of a user specified region of interest while avoiding a collision between its robot arm and another robot arm.

In block 4001, the method receives information of a user specified region of interest at the work site. When the user is viewing the work site on the display 1051, the region of interest is specified relative to an image of the work site being displayed at the time on the display 1051. The images being displayed on the display 1051 may have been derived from images captured by a camera 1003 such as a stereoscopic endoscope. Alternatively, they may have been derived from images captured by a second image capturing device 1005 such as an ultrasound probe. Alternatively, the images being displayed on the display 1051 may include both images derived from those captured by a camera 1003 and images derived from those captured by a second image capturing device 1005 by registering and superimposing the images.

As an example of one way for the user to specify the region of interest relative to the image being displayed at the time is to use a telestrator to draw a closed curve around the region of interest on a telestration screen which is displaying the same image being displayed at the time on the display 1051. For details on such a telestrator see U.S. Published Application No. 2007/0167702 A1 entitled "Medical robotic system providing three-dimensional telestration," which is incorporated herein by reference. As another example, the user may specify the region of interest by simply using an input device such as a mouse to control movement of a cursor on the display 1051 so that the path of the cursor defines the region of interest. As another example of a way for the user to specify the region of interest, the user may use a gaze tracker and a user controlled switch to indicate when the user's current gaze point on the display 1051 is to specify a center of a region of interest. In this case, the shape of the region of interest may be predefined or it may be determined by the shape of an object upon which the user is currently gazing. As yet another example of a way for the user to specify a region of interest, the user may telerobotically control movement of a working end of the manipulatable device so that it touches an object at the work site to indicate that the region of interest should be the object that has been touched.

In block 4002, the method receives information of the initial arm configurations and base positions of the image capturing device robot arm and a manipulatable device robot arm. Information of the initial arm configurations may be provided by information of their construction and information of their joint positions which is received from a plurality of sensors of the robot arms. Information of the base positions in the world reference frame may be provided by external sensors which provide such information. One example of such an external sensor is an optical sensor that is used in an optical tracking system. Another example is a pressure transducer that is one of an array of pressure transducers strategically placed at known positions on the floor of the work site.

In block 4003, the method determines a set-up position for the image capturing device so that it is properly positioned to capture the requested images of the user specified region of interest. In order to do this, the method first translates the region of interest from the display reference frame to an image capturing device reference frame using a previously determined transform and information received in block 4002. It then translates the region of interest from the image capturing device reference frame to the world reference frame using a previously determined transform and information received in block 4002. With the region of interest known in the world reference frame, the method then determines a set-up position from which the image capturing device may capture the requested images of the user specified region of interest without colliding with the initial position in the world reference frame of the manipulatable device robot arm.

In block 4004, the method determines a plan of motion for the image capturing device to capture the requested images of the user specified region of interest. When the image capturing device is the image capturing device 3020 of FIG. 12, the plan of motion may comprise planned movement of the links 1102, 1103, the wrist 1104 and the C-arm 1105.

In block 4005, the method commands movement of the image capturing device to its set-up position after receiving a command to do so from the user. When the image capturing device is the image capturing device 1116, 1117 of the Image Capturing System 3020 of FIG. 12, the commanded movement typically entails rotating the carousel joint 1108 so that the robot arm 1101 is facing the region of interest and rotating the shoulder joint 1109, elbow joint 1110, roll joint 1111, pitch joint 1112, and yaw joint 1121 so that the X-ray source 1117 and X-ray detector 1116 (i.e., the image capturing device) are properly positioned to start capturing the requested images of the user specified region of interest.

In block 4006, the method commands incremental movement of the image capturing device in accordance with the plan of motion while avoiding a collision between the image capturing device robot arm and the manipulatable device robot arm. Additional details of tasks performed by the method in block 4006 are described in reference to FIG. 6.

In block 4007, the method determines whether the plan of motion is completed. If the determination in block 4007 is NO, then the method jumps back to block 4006 to command another incremental movement of the image capturing device according to the plan of motion while avoiding a collision between the image capturing device robot arm and the manipulatable device robot arm.

On the other hand, if the determination in block 4007 is YES, then in block 4008, the method commands the image capturing device to move back to its initial position or a predefined parking position upon receiving a command to do so from the user, so that it is out of the way and presents no further risk of collision with the manipulatable device robot arm.

FIG. 6 illustrates, as an example, a flow diagram of a method for performing block 4006 of the method 4000. To supplement the description, FIG. 7 illustrates a block diagram of a portion of a robotic system which is used for collision avoidance between two independently operated robot arms. In the example illustrated by FIG. 7, a manipulatable device robot arm simulator 6003, an imminent collision detector 6021, an image capturing device robot arm simulator 6013, and an incremental motion generator 6004 are preferably implemented in a conventional manner by a processor executing program code.

In block 4201, the method receives a movement command for the manipulatable device robot arm. For example, referring to FIG. 7, the output of the manipulatable device controller 6011 provides joint commands for the manipulatable device robot arm actuators 6012.

In block 4202, the method determines the position and configuration for the manipulatable device robot arm. For example, referring to FIG. 7, the manipulatable device robot arm simulator unit 6003 generates information of the position and configuration for the manipulatable device robot arm using the joint commands from the manipulatable device controller 6011 and prior knowledge of the construction of the manipulatable device robot arm.

In block 4203, the method determines a desired incremental movement of the image capturing device. For example, referring to FIG. 7, the incremental motion generator 6004 generates a desired incremental movement of the image capturing device using information of the plan of motion determined in block 4004 of FIG. 5 and stored in memory 6005. The desired incremental movement in this case depends upon a desired velocity for the movement of the image capturing device and a process cycle period for looping through blocks 4006-4007 of FIG. 5.

In block 4204, the method determines the position and configuration for the image capturing device robot arm. For example, referring to FIG. 7, the image capturing device robot arm simulator unit 6013 generates information of the position and configuration for the image capturing device robot arm using the desired incremental motion commands provided by the incremental motion generator 6004, knowledge of the current position and configuration of the image capturing device robot arm, and prior knowledge of the construction of the image capturing device robot arm.

In block 4205, the method determines whether an imminent collision is threatened between the image capturing device robot arm and the manipulatable device robot arm in a similar manner as performed in block 2008 of FIG. 3. For example, referring to FIG. 7, the imminent collision detector 6021 determines whether a collision between the two arms is imminent by using the information provided by the robot arm simulators 6003, 6013 for the current process cycle and previous process cycles. By using time series information, not only can the trajectories of the two robot arms be predicted, but the rates at which they are moving may be estimated. With this information, a collision prediction may be made. When the predicted collision is within a specified time period, then the collision is considered to be imminent, requiring immediate action.

If the determination in block 4205 is NO, then in block 4206, the method commands the image capturing device robot arm to move according to the desired incremental movement. On the other hand, if the determination in block 4205 is YES, then in block 4207, the method modifies the incremental movement command to avoid the imminent collision, using as examples, one of the actions described in reference to block 2009 of FIG. 3. For example, after the imminent collision detector 6021 has determined that a collision between the image capturing device robot arm and the manipulatable device robot arm is imminent, it sends an indication of such to the manipulatable device controller 6011, which in turn, relays the indication to the image capturing device controller 6001 so that it can take corrective action to avoid the collision.

Some embodiments of the control units 1021-1025 and/or 3021 may include non-transient, tangible, machine readable media that include executable code that when run by one or more processors may cause the one or more processors (e.g., the processing units of control units 1021-1025 and/or 3021) to perform the processes of methods 2000, 2500, 4000, and/or 9000 as described above. Some common forms of machine readable media that may include the processes of methods 2000, 2500, 4000, and/or 9000 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although the various aspects of the present invention have been described with respect to a preferred embodiment, it will be understood that the invention is entitled to full protection within the full scope of the appended claims.

What is claimed is:

1. A movement control system comprising:
 a controller comprising:
  one or more processors; and
  memory coupled to the one or more processors;
 wherein:
  the movement control system is coupled to a computer-assisted device having a first movable arm coupled to a manipulatable device having a working end and a second movable arm coupled to an image capturing device separate from the computer-assisted device; and
  the controller is configured to:
   determine, based on at least one image of the working end received from the image capturing device, a pose of the working end in a common reference frame;
   determine a first movable arm position and a first movable arm trajectory for the first movable arm in the common reference frame;
   determine a second movable arm position and a second movable arm trajectory for the second movable arm in the common reference frame;
   based on the first movable arm position, the first movable arm trajectory, the second movable arm position, and the second movable arm trajectory, determine whether motion of the first movable arm, motion of the second movable arm, or motions of the first and second movable arms together will result in an undesirable relationship between the first and second movable arms; and
   send a first movement command to the first movable arm or the second movable arm to avoid the undesirable relationship.

2. The movement control system of claim 1 wherein:
 the common reference frame is a reference frame of the image capturing device; and the controller is further configured to determine the first movable arm position in the common reference frame further based on the pose of the working end in the common reference frame.

3. The movement control system of claim 1, wherein:
the common reference frame is a reference frame of the computer-assisted device determined based on a pose of the working end; and
the controller is further configured to:
determine the second movable arm position in a reference frame of the image capturing device;
determine a position and an orientation of the working end in the reference frame of the image capturing device; and
transform the second movable arm position and the pose of the working end from the reference frame of the image capturing device to the common reference frame.

4. The movement control system of claim 1, wherein:
the at least one image of the working end comprises a plurality of two-dimensional images from the image capturing device; and
the controller is further configured to determine the pose of the working end from the two-dimensional images even when the working end of the manipulatable device is occluded by one or more objects disposed between the image capturing device and the working end of the manipulatable device.

5. The movement control system of claim 1, further comprising:
a viewer adapted to display a second image of a work space of the working end of the manipulatable device; and
an input unit configured to receive information of a user specified region of interest within the second image being displayed on the viewer;
wherein the controller is further configured to send second movement commands to the second movable arm so that the image capturing device captures images of the user specified region of interest.

6. The movement control system of claim 1, wherein the controller determines the first movable arm position and the first movable arm trajectory based on sensed positions of joints of the first movable arm and known geometries of the joints and links of the first movable arm.

7. The movement control system of claim 1, wherein the controller determines the second movable arm position and the second movable arm trajectory based on sensed positions of joints of the second movable arm and known geometries of the joints and links of the second movable arm.

8. The movement control system of claim 1, wherein:
the first movable arm has redundant degrees of freedom so that for each controllable pose of the working end of the manipulatable device there are a first plurality of possible positions and orientations for the first movable arm;
the second movable arm has redundant degrees of freedom so that for each controllable position and orientation of the image capturing device there are a second plurality of possible positions and orientations for the second movable arm; and
the first movement command sent to the first movable arm or the second movable arm directs the first movable arm to move to one of the first plurality of possible positions and orientations or directs the second movable arm to move to one of the second plurality of possible positions and orientations that avoid the undesirable relationship.

9. The movement control system of claim 8, wherein the controller is further configured to:
determine which one of the first movable arm and the second movable arm is to be sent the first movement command based on differences between the first movable arm position and the first plurality of possible positions and orientations and differences between the second movable arm position and the second plurality of possible positions and orientations; and
the determination of which one of the first movable arm and the second movable arm is to be sent the first movement command is made so as to minimize a cost function.

10. The movement control system of claim 9, wherein the cost function is based on an inverse square of a minimum distance between the first movable arm and the second movable arm.

11. The movement control system of claim 9, wherein the cost function is based on an average of an inverse square of distances between links of the first movable arm and links of the second movable arm.

12. The movement control system of claim 9, wherein the cost function is based on virtual potential fields applied to first links and first joints of the first movable arm and second links and second joints of the second movable arm.

13. The movement control system of claim 1, wherein the undesirable relationship is selected from a group consisting of a collision between the first movable arm and the second movable arm, too close a proximity between the first movable arm and the second movable arm, and obstruction of a region of interest of the image capturing device by the first movable arm.

14. A method of controlling movement in a medical system, the method comprising:
determining, based on at least one image of a working end of a manipulatable device coupled to a first articulated arm of a computer-assisted device, a pose of the working end in a common reference frame;
determining, based on first configurations of the first articulated arm, a first arm position and a first arm trajectory for the first articulated arm in the common reference frame;
determining, based on second configurations of a second articulated arm of an image capturing device separate from the computer-assisted device, a second arm position and a second arm trajectory for the second articulated arm in the common reference frame;
based on the first arm position, the first arm trajectory, the second arm position, and the second arm trajectory, determining whether motion of the first articulated arm, motion of the second articulated arm, or motions of the first and second articulated arms together will result in an undesirable relationship between the first and second articulated arms; and
sending a first movement command to the first articulated arm or the second articulated arm to avoid the undesirable relationship.

15. The method of claim 14, wherein:
the common reference frame is a reference frame of the image capturing device; and
the method further comprises determining the first arm position in the common reference frame further based on the pose of the working end in the common reference frame.

16. The method of claim 14, wherein:
the common reference frame is a reference frame of the computer-assisted device; and
the method further comprises:
  determining the second arm position in a reference frame of the image capturing device;
  determining the pose of the working end in the reference frame of the image capturing device; and
  transforming the second arm position and the pose of the working end from the reference frame of the image capturing device to the common reference frame.

17. The method of claim 14, wherein:
the at least one image of the working end comprises a plurality of two-dimensional images from the image capturing device; and
the method further comprises determining the pose of the working end from the two-dimensional images even when the working end is occluded by one or more objects disposed between the image capturing device and the working end.

18. The method of claim 14, further comprising determining the first movement command so as to minimize a cost function.

19. A medical system comprising:
a computer-assisted medical device having a first movable arm coupled to a manipulatable device having a working end;
a medical image capturing device coupled a second movable arm separate from the computer-assisted medical device; and
a movement control system coupled to the first movable arm and the second movable arm;
wherein the movement control system is configured to:
  determine, based on at least one image of the working end received from the medical image capturing device, a pose of the working end in a common reference frame;
  determine a first movable arm position and a first movable arm trajectory for the first movable arm in the common reference frame;
  determine a second movable arm position and a second movable arm trajectory for the second movable arm in the common reference frame;
  based on the first movable arm position, the first movable arm trajectory, the second movable arm position, and the second movable arm trajectory, determine whether motion of the first movable arm, motion of the second movable arm, or motions of the first and second movable arms together will result in an undesirable relationship between the first and second movable arms; and
  send a first movement command to the first movable arm or the second movable arm to avoid the undesirable relationship.

20. The medical system of claim 19, further comprising:
a viewer adapted to display a second image of a work space of the working end of the manipulatable device; and
an input unit configured to receive information of a user specified region of interest within the second image being displayed on the viewer;
wherein the movement control system is further configured to send second movement commands to the second movable arm so that the image capturing device captures images of the user specified region of interest.

* * * * *